US008922760B2

(12) United States Patent
Kajioka

(10) Patent No.: US 8,922,760 B2
(45) Date of Patent: Dec. 30, 2014

(54) DEFOCUSED OPTICAL ROTATION MEASUREMENT APPARATUS, OPTICAL ROTATION MEASUREMENT METHOD AND DEFOCUSED OPTICAL FIBER SYSTEM

(75) Inventor: Hiroshi Kajioka, Tokyo (JP)

(73) Assignee: Global Fiberoptics, Ltd., Tokyo (JP)

( * ) Notice: Subject to any disclaimer, the term of this patent is extended or adjusted under 35 U.S.C. 154(b) by 213 days.

(21) Appl. No.: 13/698,988

(22) PCT Filed: May 18, 2011

(86) PCT No.: PCT/JP2011/061442
§ 371 (c)(1),
(2), (4) Date: Feb. 1, 2013

(87) PCT Pub. No.: WO2011/145652
PCT Pub. Date: Nov. 24, 2011

(65) Prior Publication Data
US 2013/0128262 A1  May 23, 2013

(30) Foreign Application Priority Data

May 19, 2010  (JP) .................................. 2010-128301
Nov. 26, 2010  (JP) .................................. 2010-264353

(51) Int. Cl.
| G01N 33/48 | (2006.01) |
| G01N 21/55 | (2014.01) |
| A61B 5/1455 | (2006.01) |
| G01N 21/59 | (2006.01) |
| G01N 21/21 | (2006.01) |
| A61B 5/145 | (2006.01) |

(52) U.S. Cl.
CPC ............ *G01N 21/55* (2013.01); *G01N 2201/08* (2013.01); *A61B 5/1455* (2013.01); *G01N 21/59* (2013.01); *A61B 5/14558* (2013.01); *G01N 21/21* (2013.01); *A61B 5/14532* (2013.01)
USPC .......................................................... 356/39

(58) Field of Classification Search
CPC ... G01N 33/49; G01N 15/05; G01N 15/1434; A61B 5/14532; A61B 5/1455

USPC ............................................................ 356/39
See application file for complete search history.

(56) References Cited

U.S. PATENT DOCUMENTS

2008/0019224 A1 * 1/2008 Ishibashi .................... 369/30.03

FOREIGN PATENT DOCUMENTS

| JP | 07183186 A * 7/1995 |
| JP | 10-267831 A  10/1998 |

(Continued)

OTHER PUBLICATIONS

Masayuki Yokota et al., "Glucose sensor using a flint glass Fiber Faraday rotator", Proceedings of 31st Meetings on Lightwave Sensing Technology, LST31-8, pp. 51-56, Jun. 2003.

(Continued)

*Primary Examiner* — Tarifur Chowdhury
*Assistant Examiner* — Md Rahman
(74) *Attorney, Agent, or Firm* — Smith Patent Office

(57) ABSTRACT

There is provided an optical rotation measurement apparatus and a measuring system which are user-friendly, capable of measuring glucose concentration in drawn blood and living bodies with high accuracy in real time such that it is available for use at an actual medical site without depending on a reagent, and capable of measuring glucose concentration in a living body noninvasively with high accuracy, a new polarized light converting optical system that can be used for the measuring system, and an optical rotation measurement method using the optical system.

The problems are resolved by inserting a non-reciprocal optical system sandwiching a specimen in an optical fiber ring interferometer, using input/output optical fibers of the non-reciprocal optical system, which are comprised of a large core diameter low NA single mode optical fiber, as an input/output part, connected via a mode-matching unit to a small core diameter and high NA polarization preserving fiber as a transmission part, and employing a defocused configuration without deploying the optical fiber ends at focal points of lenses.

19 Claims, 12 Drawing Sheets

(56) References Cited

FOREIGN PATENT DOCUMENTS

| | | |
|---|---|---|
| JP | 2004-113434 A | 4/2004 |
| JP | 2004-138864 A | 5/2004 |
| JP | 2004-313554 A | 11/2004 |
| JP | 2005-274380 A | 10/2005 |
| JP | 2006-323027 A | 11/2006 |
| JP | 2007-093289 A | 4/2007 |
| JP | 2008-032993 A | 2/2008 |
| JP | 2008-102009 A | 5/2008 |

OTHER PUBLICATIONS

Hiroshi Kajioka et al., "Development of Optical Fiber Gyroscope", Proceedings of 3rd Meeting on Lightwave Sensing Technology, Lightwave Sensing Technology Research Group, Japan Society of Applied Physics, LST 3-9, pp. 55-62, Jun. 1989.

International Search Report, directed to International Patent Application No. PCT/JP2011/061442, 7 pages including English translation.

* cited by examiner

DEFOCUSED OPTICAL ROTATION MEASUREMENT APPARATUS, OPTICAL ROTATION MEASUREMENT METHOD AND DEFOCUSED OPTICAL FIBER SYSTEM

TECHNICAL FIELD

The present invention relates to a defocused optical rotation measurement apparatus for a light-scattering specimen as a specimen for optical rotation measurement such as a drawn blood, blood serum, or a living body, a defocused optical fiber optical system that can be employed in an optical rotation system, and an optical rotation measurement method using the defocused optical fiber optical system. More specifically, it relates to a defocused optical rotation measurement apparatus capable of measuring glucose concentration in the specimen for optical rotation measurement, and measure glucose composition concentration in the specimen for optical rotation measurement with high accuracy by irradiating a laser beam on human blood, finger, ear, skin, and the like, and measuring the transmitted light and/or reflected light thereof, a defocused optical fiber optical system and an optical rotation measurement method using the defocused optical fiber optical system.

BACKGROUND ART

A first method known as a method of measuring glucose concentration in blood is a method of irradiating an infrared laser beam on a part of a living body such as a finger, dispersing the scattered light from a blood vessel, and measuring glucose in the blood, as described in Patent Document 1. This method utilizes the fact that the scattered light decreases in proportion to the glucose concentration. This method, however, has a problem that the light intensity of the scattered light is dependent on temperature, moisture and oil component of the skin etc., and is therefore not popular in actuality.

A second method is a method of making the polarized component that is orthogonal to the optical rotation component transmit, and then measuring birefringence thereof in an open loop, as described in Non-patent Document 1 and Patent Document 2, etc. However, according to this method, it is impossible to measure approximately 10 mm-thick glucose with a healthy person's blood sugar level of approximately 0.1 g/dL (deciliter) in blood or a living body such as a finger because of a large measurement error.

A third method is a method of measuring using the birefringence measurement apparatus described in Patent Document 3. This method, in the same manner as the present invention, measures optical rotation of a specimen by providing an opposing collimator optical system in the ring of a ring interferometer comprised of polarization preserving fibers, making a collimated beam propagate within the specimen, and measuring the phase difference between the clockwise and the counter-clockwise propagating polarized light. This method allows measurement of approximately 10 mm-thick glucose with a healthy person's blood sugar level of 0.1 g/dL, placed in a glass cell with sufficient accuracy.

FIG. 23 is a view illustrating a conventional optical system where a light-scattering specimen is inserted between the opposing collimators. Lenses 3-1 and 3-2 are deployed at positions at focal distances 5-1 and 5-2 of the lenses 3-1 and 3-2 from ends of a pair of single mode (referred to as SM hereafter) optical fibers 1-1 and 1-2 having ferrules 2-1 and 2-2, respectively, thereby constituting an opposing collimator optical system, a light-scattering specimen 4 is placed therebetween, and optical rotation of the light-scattering specimen 4 is measured. As the best method for increasing measurement accuracy, it has a structure where ends of respective optical fibers are deployed at the focal positions of the lenses, respectively, so as to form the opposing collimators, an optical signal emitted from the end of one of the optical fibers is collimated by the lenses and irradiated onto the light-scattering specimen 4, and the optical signal transmitted through the light-scattering specimen 4 is coupled with the other optical fiber. However, when approximately 1.5 mm-thick webbing between fingers is inserted between the opposing collimators of FIG. 23, scattering loss of the living body is great, and optical rotation cannot be measured.

This is because while insertion loss of the single mode optical fiber opposing collimator optical system is normally approximately 0.5 dB, insertion loss is 80 dB or greater if the living body is inserted therewithin.

FIG. 24 shows theoretical calculation results of beam angle dependency in the case where focal distance f of the lenses of the opposing collimators using the SM optical fibers for wavelength of 850 nm is 2.5 mm and distance between the lenses is 30 mm, where in the drawing, the horizontal axis gives collimator angle (unit: degree) or angle of incoming and outgoing beams to and from the collimators, and the vertical axis gives loss (unit: dB). This shows that the coupling loss increases by 50 dB or greater if the beam angle deviates approximately zero to 0.3 degrees. Therefore, the reason that the insertion loss becomes 80 dB or greater when finger webbing is actually sandwiched by single mode optical fiber opposing collimator optical systems with lenses is considered that the light beam collimated by the lenses is scattered randomly within the living body, thereby changing the beam propagating angle.

Until now, there has been much attempt in development of optical measurement apparatuss for measuring glucose concentration in living bodies and drawn blood with high accuracy as can be seen from the above. However, the real situation is that it is very difficult to measure the glucose concentration in living bodies and drawn blood with high accuracy, and a measurement apparatus for measuring glucose concentration in living bodies and drawn blood is not developed yet, although it is used for measurement of sugar content in fruit, and thereby measurement of glucose concentration in living bodies and drawn blood must rely on methods using reagents.

PRIOR ART DOCUMENTS

Patent Documents

Patent Document 1: JP 2004-313554A
Patent Document 2: JP 2007-093289A
Patent Document 3: JP 2005-274380A Non-Patent Documents Non-patent Document 1: Yokota Masayuki et el., "Glucose sensor using a lead glass fiber polarization modulation device", The 31st lightwave sensing technical study meeting LST 31-8, PP. 51-56, June, 2003.
Non-patent Document 2: Kajioka and Oho, "Development of optical fiber gyro", The third lightwave sensing technical study meeting, LST 3-9, PP. 55-62, June, 1989.

DISCLOSURE OF THE INVENTION

Problem to be Solved by the Invention

As mentioned above, an optical measurement apparatus for measuring the glucose concentration in living bodies and drawn blood with high accuracy has not been practically applied yet. The present invention has been devised in light of the situation give above, and an object of the present invention is to provide an optical rotation measurement apparatus and measuring system, which are user-friendly, capable of measuring the glucose concentration in drawn blood and living bodies with high accuracy in real time such that it is available for use at an actual medical site without depending on a reagent, and capable of measuring the glucose concentration in living bodies noninvasively with high accuracy, and further to provide a new polarized light converting optical system that can be used for the measuring system, and an optical rotation measurement method using the optical system.

Means of Solving the Problem

According to a well-known technical idea for reducing coupling loss in the optical fiber optical system in which optical fibers, each having a lens on the tip end face, sandwich a subject to be measured and oppose each other, so as to optically couple themselves from one to the other on the optical path of an optical signal, a collimator optical system with ends of opposing optical fibers deployed at the focal positions of the lenses is preferable. However, according to the inventor's experimental study results, this method cannot resolve the problem of the present invention.

The present invention differs from the conventional technological idea, and resolves the problem by employing a polarized light converting optical system according to a completely new technological idea of shifting the ends of the optical fibers from the focal positions of the lenses. Moreover, a mode-matching unit is introduced to the polarized light converting optical system, so as to provide a lower coupling loss of the optical system not expected so far in which a light-scattering specimen, such as a living body, is sandwiched by optical fibers. Embodiments of the present invention will be described in detail hereinafter.

According to a first aspect of the present invention to solve the problem (the aspect 1 hereafter), a defocused optical rotation measurement apparatus for measuring for optical information on optical rotation of a specimen by deploying single mode optical fibers, each having a lens deployed at a tip end, along an optical path of an optical signal, facing each other and sandwiching a specimen for optical rotation measurement (referred to as specimen hereafter), such as a light-scattering specimen, irradiating on the specimen an optical signal emitted from an end of one of the single mode optical fibers having a lens at the tip end, irradiating an optical signal having passed through the specimen or an optical signal reflected by the specimen on an end of the other single mode optical fiber having a lens at the tip end; wherein a lens (lens deployed at an output part of the optical fibers for an optical signal irradiated on the specimen and/or an inlet part for an optical signal from the specimen is simply referred to as output part lens hereafter) deployed at an output part of the one single mode optical fiber for an optical signal irradiated on the specimen and/or an inlet part for an optical signal from the specimen, and the output part lens deployed at an inlet part of the other single mode optical fiber for an optical signal from the specimen and/or an output part for an optical signal irradiated on the specimen are deployed along the optical path of the optical signal, and at least either an end of the one single mode optical fiber or an end of the other single mode optical fiber forms a defocused optical fiber optical system not deployed at a focal point of the output part lens of said single mode optical fiber.

A second aspect of the present invention based on the first aspect (hereinafter referred to as the aspect 2) is the defocused optical rotation measurement apparatus, wherein at least either numerical aperture (referred to as NA hereafter) of the one single mode optical fiber or NA of the other single mode optical fiber is 0.07 or less.

A third aspect of the present invention based on the aspect 1 or 2 (hereinafter referred to as the aspect 3) is the defocused optical rotation measurement apparatus, wherein the end of the one single mode optical fiber and the end of the other single mode optical fiber are deployed at positions closer to the output part lenses of the optical fibers than focal points of the output part lenses.

A fourth aspect of the present invention based on the aspect 1 or 2 (hereinafter referred to as the aspect 4) is the defocused optical rotation measurement apparatus, wherein the end of the one single mode optical fiber and the end of the other single mode optical fiber are deployed at positions further away from the output part lenses of the optical fibers than focal points of the output part lenses.

A fifth aspect of the present invention based on any one of the aspects 1 to 4 (hereinafter referred to as the aspect 5) is the defocused optical rotation measurement apparatus, wherein the tip end of the single mode optical fiber and the output part lens of the optical fiber are fixed to each other.

A sixth aspect of the present invention based on any one of the aspects 1 to 5 (hereinafter referred to as the aspect 6) is the defocused optical rotation measurement apparatus, wherein at least either one single mode optical fiber or the other single mode optical fiber has a Faraday rotary element arranged between the specimen and the single mode optical fiber end.

A seventh aspect of the present invention based on any one of the aspects 1 to 6 (hereinafter referred to as the aspect 7) is the defocused optical rotation measurement apparatus, wherein at least either the one single mode optical fiber or the other single mode optical fiber has a ¼ wave plate and a polarizer arranged between the specimen and the single mode optical fiber end.

An eighth aspect of the present invention based on any one of the aspects 1 to 7 (hereinafter referred to as the aspect 8) is the defocused optical rotation measurement apparatus, the one single mode optical fiber and the other single mode optical fiber are polarization preserving fibers; a polarizer, a Faraday rotary element, and a ¼ wave plate are arranged between each of the optical fiber ends and the specimen; an optical signal of the same natural polarization mode (namely, polarization output mode) is emitted from both of the polarization preserving fibers, and enters the specimen as either a clockwise propagating light or a counterclockwise propagating light from one of the inlet sides of the specimen, and enters the specimen as either a clockwise propagating light or a counterclockwise propagating light from the other one of the inlet sides of the specimen, and directions of the polarizer, the Faraday rotary element, and the ¼ wave plate and a natural polarization direction of the polarization preserving fibers are set such that the lights are coupled with the polarization preserving fibers on an optical path in a polarization mode equivalent to the polarization output mode.

A ninth aspect of the present invention based on any one of the aspects 1 to 8 (hereinafter referred to as the aspect 9) is the defocused optical rotation measurement apparatus, wherein the defocused optical rotation measurement apparatus measures optical rotation of the specimen by constituting an optical ring path for a ring light interference system by the specimen, the defocused optical fiber optical system, and the polarization preserving fibers, and measuring phase difference of the light propagating along the optical ring path in both directions that occurs due to the specimen.

A tenth aspect of the present invention based on the aspect 9 (hereinafter referred to as the aspect 10) is the defocused optical rotation measurement apparatus, wherein the defocused optical rotation measurement apparatus is comprised so as to propagate polarized light as a clockwise propagating optical signal and polarized light as a counterclockwise propagating optical signal along the optical ring path of the ring interferometer, propagate polarized light as a clockwise propagating optical signal and polarized light as a counterclockwise propagating optical signal respectively as a clockwise propagating optical signal and a counterclockwise propagating optical signal through the same optical fiber portion of the optical ring path of the ring interferometer in the same natural linear polarization mode, and propagate a clockwise propagating optical signal and a counterclockwise propagating optical signal through the specimen as orthogonal circularly polarized lights.

A eleventh aspect of the present invention based on any one of the aspects 1 to 10 (hereinafter referred to as the aspect 11) is the defocused optical rotation measurement apparatus, wherein a mechanism for scanning the specimen orthogonally to the optical path.

A twelfth aspect of the present invention based on any one of the aspects 1 to 11 (hereinafter referred to as the aspect 12) is the defocused optical rotation measurement apparatus, wherein the specimen is a part of a living body, and the optical rotation measurement apparatus further comprises, as a detecting means for the optical rotation of the optical signals, means for detecting the phase difference in sync with a technically applied signal for periodically varying dimensions of the part of the living body, such pulse beats of the living body or thickness of a region to be measured, so as to measure optical information on optical rotation of the specimen.

A thirteenth aspect of the present invention based on any one of the aspects 1 to 12 (hereinafter referred to as the aspect 13) is the defocused optical rotation measurement apparatus, wherein the specimen is a part of a living body, the defocused optical rotation measurement apparatus comprises measuring terminals for sandwiching a portion for measuring for optical information on optical rotation of the specimen, and the tip ends of the optical fibers are held by the measuring terminals.

A fourteenth aspect of the present invention based on any one of the aspects 1 to 13 (hereinafter referred to as the aspect 14) is the defocused optical rotation measurement apparatus, which further comprises inter-lens distance adjusting means for changing distance between the output part lens of the one single mode optical fiber and the output part lens of the other single mode optical fiber.

A fifteenth aspect of the present invention based on any one of the aspects 1 to 14 (hereinafter referred to as the aspect 15) is the defocused optical rotation measurement apparatus, wherein at least either one single mode optical fiber or the other single mode optical fiber is a single mode optical fiber connecting via a mode-matching unit a first optical fiber and a second optical fiber differing in core diameter, the first optical fiber is a comparatively smaller core diameter high NA polarization preserving fiber and the second optical fiber is a comparatively larger core diameter low NA polarization preserving fiber, the second optical fiber of the single mode optical fibers is deployed closer to the specimen along the optical path than the first optical fiber, and the output part lens is deployed along the optical path of the optical signal in the vicinity of the end of the second optical fiber closer to the specimen.

A sixteenth aspect of the present invention based on any one of the aspects 1 to 15 (hereinafter referred to as the aspect 16) is the defocused optical rotation measurement apparatus, wherein the one optical fiber and the other optical fiber facing each other and sandwiching the specimen along the optical path of the optical signals are the same type of optical fiber.

A seventeenth aspect of the present invention based on any one of the aspects 1 to 16 (hereinafter referred to as the aspect 17) is the defocused optical rotation measurement apparatus, wherein the optical fibers facing each other and sandwiching the specimen along the optical path of the optical signals are so-called double-cladding optical fibers.

An eighteenth aspect of the present invention based on any one of the aspects 1 to 17 (hereinafter referred to as the aspect 18) is the defocused optical rotation measurement apparatus, wherein at least either an expanded-core fiber or a reduced-core fiber is used in the mode-matching unit.

A nineteenth aspect of the present invention based on any one of the aspects 1 to 18 (hereinafter referred to as the aspect 19) is the defocused optical rotation measurement apparatus, wherein distance between the output part lens of the one single mode optical fiber and the output part lens of the other single mode optical fiber is shorter than 3 mm.

A twentieth aspect of the present invention based on any one of the aspects 1 to 19 (hereinafter referred to as the aspect 20) is the defocused optical rotation measurement apparatus, wherein both of the defocused optical fiber optical systems facing each other and sandwiching the specimen along the optical path of the optical signal and has the polarizer, the Faraday rotary element, the ¼ wave plate, and the output part lenses deployed at the optical fiber ends are on the same side of an optical signal inlet side, and the ¼ wave plate is deployed between the defocused optical fiber optical systems and the specimen.

According to a twenty-first aspect of the present invention to solve the problem (hereinafter as the aspect 21), a defocused optical fiber optical system for measuring for optical information on optical rotation of a specimen by deploying single mode optical fibers, each having a lens deployed at a tip end, along an optical path of an optical signal, facing each other and sandwiching a specimen for optical rotation measurement (referred to as specimen hereafter), such as a light-scattering specimen, irradiating on the specimen an optical signal emitted from an end of one single mode optical fiber having a lens at the tip end, irradiating an optical signal having passed through the specimen or an optical signal reflected by the specimen on an end of the other single mode optical fiber having a lens at the tip end; wherein a lens (lens deployed at an output part of the optical fibers for an optical signal irradiated on the specimen and/or an inlet part for an optical signal from the specimen is simply referred to as output part lens hereafter) deployed at an output part of the one of the single mode optical fibers for an optical signal irradiated on the specimen and/or an inlet part for an optical signal from the specimen, and the output part lens deployed at an inlet part of the other one of the single mode optical fibers for an optical signal from the specimen and/or an output part for an optical signal irradiated on the specimen are deployed along the optical path of the optical signal, and at least either an end of the one single mode optical fiber or an end of the other single mode optical fiber forms a defocused optical fiber optical system not deployed at a focal point of the output part lens of said single mode optical fiber.

A twenty-second aspect of the present invention based on the aspect 21 (hereinafter referred to as the aspect 22) is the defocused optical fiber optical system, wherein at least either numerical aperture (referred to as NA hereafter) of the one single mode optical fiber or NA of the other single mode optical fiber is 0.07 or less.

A twenty-third aspect of the present invention based on the aspect 21 or 22 (hereinafter referred to as the aspect 23) is the defocused optical fiber optical system, wherein the end of the one single mode optical fiber and the end of the other single mode optical fiber are deployed at positions closer to the output part lenses of the optical fibers than focal points of the output part lenses.

A twenty-fourth aspect of the present invention based on the aspect 21 or 22 (hereinafter referred to as the aspect 24) is the defocused optical fiber optical system, wherein the end of the one single mode optical fiber and the end of the other single mode optical fiber are deployed at positions further away from the output part lenses of the optical fibers than focal points of the output part lenses.

A twenty-fifth aspect of the present invention based on any one of the aspects 21 to 24 (hereinafter referred to as the aspect 25) is the defocused optical fiber optical system, wherein the tip end of the single mode optical fiber and the output part lens of the optical fiber are fixed to each other.

A twenty-sixth aspect of the present invention based on any one of the aspects 21 to 25 (hereinafter referred to as the aspect 26) is the defocused optical fiber optical system, wherein at least either one single mode optical fiber or the other single mode optical fiber has a Faraday rotary element arranged between the specimen and the single mode optical fiber end.

A twenty-seventh aspect of the present invention based on any one of the aspects 21 to 26 (hereinafter referred to as the aspect 27) is the defocused optical fiber optical system, wherein at least either the one single mode optical fiber or the other single mode optical fiber has a ¼ wave plate and a polarizer arranged between the specimen and the single mode optical fiber end.

A twenty-eighth aspect of the present invention based on any one of the aspects 21 to 27 (hereinafter referred to as the aspect 28) is the defocused optical fiber optical system, wherein the one single mode optical fiber and the other single mode optical fiber are polarization preserving fibers; a polarizer, a Faraday rotary element, and a ¼ wave plate are arranged between each of the optical fiber ends and the specimen; an optical signal of the same natural polarization mode (namely, polarization output mode) is emitted from both of the polarization preserving fibers, and enters the specimen as either a clockwise propagating light or a counterclockwise propagating light from one of the inlet sides of the specimen, and enters the specimen as either a clockwise propagating light or a counterclockwise propagating light from the other one of the inlet sides of the specimen, and directions of the polarizer, the Faraday rotary element, and the ¼ wave plate and a natural polarization direction of the polarization preserving fibers are set such that the lights are coupled with the polarization preserving fibers on an optical path in a polarization mode equivalent to the polarization output mode.

A twenty-ninth aspect of the present invention based on any one of the aspects 21 to 28 (hereinafter referred to as the aspect 29) is the defocused optical fiber optical system, wherein the defocused optical fiber optical system is employed as a component of an optical rotation measuring system for measuring optical rotation of the specimen by constituting an optical ring path for a ring light interference system by the specimen, the defocused optical fiber optical system, and the polarization preserving fibers, and measuring phase difference of the light propagating along the optical path in both directions that occurs due to the specimen.

A thirtieth aspect of the present invention based on the aspects 29 (hereinafter referred to as the aspect 30) is the defocused optical fiber optical system, wherein the defocused optical fiber optical system is comprised so as to propagate polarized light as a clockwise propagating optical signal and polarized light as a counterclockwise propagating optical signal along the optical ring path of the ring interferometer, propagate polarized light as a clockwise propagating optical signal and polarized light as a counterclockwise propagating optical signal respectively as a clockwise propagating optical signal and a counterclockwise propagating optical signal through the same optical fiber portion of the optical ring path of the ring interferometer in the same natural linear polarization mode, and propagate a clockwise propagating optical signal and a counterclockwise propagating optical signal through the specimen as orthogonal circularly polarized lights.

A thirty-first aspect of the present invention based on any one of the aspects 21 to 30 (hereinafter referred to as the aspect 31) is the defocused optical fiber optical system, which comprises a mechanism for scanning the specimen orthogonally to the optical path.

A thirty-second aspect of the present invention based on any one of the aspects 21 to 31 (hereinafter referred to as the aspect 32) is the defocused optical fiber optical system, wherein the specimen is a part of a living body, and the optical rotation measurement apparatus further comprises, as a detecting means for the optical rotation of the optical signals, means for detecting the phase difference in sync with a technically applied signal for periodically varying dimensions of the part of the living body, such pulse beats of the living body or thickness of a region to be measured, so as to measure optical information on optical rotation of the specimen.

A thirty-third aspect of the present invention based on any one of the aspects 21 to 32 (hereinafter referred to as the aspect 33) is the defocused optical fiber optical system, wherein the specimen is a part of a living body, the optical fiber optical system comprises measuring terminals for sandwiching a portion for measuring for optical information on optical rotation of the specimen, and the tip ends of the optical fibers are held by the measuring terminals.

A thirty-fourth aspect of the present invention based on any one of the aspects 21 to 33 (hereinafter referred to as the aspect 34) is the defocused optical fiber optical system, which further comprises inter-lens distance adjusting means for changing distance between the output part lens of the one single mode optical fiber and the output part lens of the other single mode optical fiber.

A thirty-fifth aspect of the present invention based on any one of the aspects 21 to 34 (hereinafter referred to as the aspect 35) is the defocused optical fiber optical system, wherein at least either one single mode optical fiber or the other single mode optical fiber is a single mode optical fiber connecting via a mode-matching unit a first optical fiber and a second optical fiber differing in core diameter, the first optical fiber is a comparatively smaller core diameter high NA polarization preserving fiber and the second optical fiber is a comparatively larger core diameter low NA polarization preserving fiber, the second optical fiber of the single mode optical fibers is deployed closer to the specimen along the optical path than the first optical fiber, and the output part lens is deployed along the optical path of the optical signal in the vicinity of the end of the second optical fiber closer to the specimen.

A thirty-sixth aspect of the present invention based on any one of the aspects 21 to 35 (hereinafter referred to as the aspect 36) is the defocused optical fiber optical system, wherein the one optical fiber and the other optical fiber facing each other and sandwiching the specimen along the optical path of the optical signals are the same type of optical fiber.

A thirty-seventh aspect of the present invention based on any one of the aspects 21 to 36 (hereinafter referred to as the aspect 37) is the defocused optical fiber optical system, wherein the optical fibers facing each other and sandwiching the specimen along the optical path of the optical signals are so-called double-cladding optical fibers.

A thirty-eighth aspect of the present invention based on any one of the aspects 21 to 37 (hereinafter referred to as the aspect 38) is the defocused optical fiber optical system, wherein at least either an expanded-core fiber or a reduced-core fiber is used in the mode-matching unit.

A thirty-ninth aspect of the present invention based on any one of the aspects 21 to 38 (hereinafter referred to as the aspect 39) is the defocused optical fiber optical system, wherein distance between the output part lens of the one single mode optical fiber and the output part lens of the other single mode optical fiber is shorter than 3 mm.

A fortieth aspect of the present invention based on any one of the aspects 21 to 39 (hereinafter referred to as the aspect 40) is the defocused optical fiber optical system, wherein both of the defocused optical fiber optical systems facing each other and sandwiching the specimen along the optical path of the optical signal and has the polarizer, the Faraday rotary element, the ¼ wave plate, and the output part lenses deployed at the optical fiber ends are on the same side of an optical signal inlet side, and the ¼ wave plate is deployed between the defocused optical fiber optical systems and the specimen.

According to a forty-first aspect of the present invention to solve the problem (hereinafter as the aspect 41), a defocused optical rotation measurement method for measuring for optical information on optical rotation of a specimen by deploying single mode optical fibers, each having a lens deployed at a tip end, along an optical path of an optical signal, facing each other and sandwiching a specimen for optical rotation measurement (referred to as specimen hereafter), such as a light-scattering specimen, irradiating on the specimen an optical signal emitted from an end of one single mode optical fiber having a lens at the tip end, irradiating an optical signal having passed through the specimen or an optical signal reflected by the specimen on an end of the other single mode optical fiber having a lens at the tip end; wherein a lens (lens deployed at an output part of the optical fibers for an optical signal irradiated on the specimen and/or an inlet part for an optical signal from the specimen is simply referred to as output part lens hereafter) deployed at an output part of the one single mode optical fiber for an optical signal irradiated on the specimen and/or an inlet part for an optical signal from the specimen, and the output part lens deployed at an inlet part of the other single mode optical fiber for an optical signal from the specimen and/or an output part for an optical signal irradiated on the specimen are deployed along the optical path of the optical signal, and at least either an end of the one single mode optical fiber or an end of the other single mode optical fiber forms a defocused optical fiber optical system not deployed at a focal point of the output part lens of said single mode optical fiber.

A forty-second aspect of the present invention based on the aspect 41 (hereinafter referred to as the aspect 42) is a defocused optical rotation measurement method, wherein at least either numerical aperture (referred to as NA hereafter) of the one single mode optical fiber or NA of the other single mode optical fiber is 0.07 or less.

A forty-third aspect of the present invention based on the aspect 41 or 42 (hereinafter referred to as the aspect 43) is the defocused optical rotation measurement method, wherein the end of the one single mode optical fiber and the end of the other single mode optical fiber are deployed at positions closer to the output part lenses of the optical fibers than focal points of the output part lenses.

A forty-fourth aspect of the present invention based on the aspect 41 or 44 (hereinafter referred to as the aspect 44) is the defocused optical rotation measurement method, wherein the end of the one single mode optical fiber and the end of the other single mode optical fiber are deployed at positions further away from the output part lenses of the optical fibers than focal points of the output part lenses.

A forty-fifth aspect of the present invention based on any one of the aspects 41 to 44 (hereinafter referred to as the aspect 45) is the defocused optical rotation measurement method, wherein a single mode optical fiber having the single mode optical fiber tip end and the output part lens of the optical fiber fixed to each other is used.

A forty-sixth aspect of the present invention based on any one of the aspects 41 to 45 (hereinafter referred to as the aspect 46) is the defocused optical rotation measurement method, wherein at least either the one single mode optical fiber or the other single mode optical fiber has a Faraday rotary element arranged between the specimen and the single mode optical fiber end.

A forty-seventh aspect of the present invention based on any one of the aspects 41 to 46 (hereinafter referred to as the aspect 47) is the defocused optical rotation measurement method, wherein at least either the one single mode optical fiber or the other single mode optical fiber has a ¼ wave plate and a polarizer arranged between the specimen and the single mode optical fiber end.

A forty-eighth aspect of the present invention based on any one of the aspects 41 to 47 (hereinafter referred to as the aspect 48) is the defocused optical rotation measurement method, wherein the one single mode optical fiber and the other single mode optical fiber are polarization preserving fibers; a polarizer, a Faraday rotary element, and a ¼ wave plate are arranged between each of the optical fiber ends and the specimen; an optical signal of the same natural polarization mode (namely, polarization output mode) is emitted from both of the polarization preserving fibers, and enters the specimen as either a clockwise propagating light or a counterclockwise propagating light from one of the inlet sides of the specimen, and enters the specimen as either a clockwise propagating light or a counterclockwise propagating light from the other one of the inlet sides of the specimen, and directions of the polarizer, the Faraday rotary element, and the ¼ wave plate and a natural polarization direction of the polarization preserving fibers are set such that the lights are coupled with the polarization preserving fibers on an optical path in a polarization mode equivalent to the polarization output mode.

A forty-ninth aspect of the present invention based on any one of the aspects 41 to 48 (hereinafter referred to as the aspect 49) is the defocused optical rotation measurement method, wherein the defocused optical rotation measuring system measures optical rotation of the specimen by constituting an optical ring path for a ring light interference system by the specimen, the defocused optical fiber optical system, and the polarization preserving fibers, and measures phase difference of the light propagating along the optical path in both directions that occurs due to the specimen.

A fiftieth aspect of the present invention based on the aspect 49 (hereinafter referred to as the aspect 50) is the defocused optical rotation measurement method, wherein the defocused optical rotation measuring system s comprised so as to propagate polarized light as a clockwise propagating optical signal and polarized light as a counterclockwise propagating optical signal along the optical ring path of the ring interferometer, propagate polarized light as a clockwise propagating optical signal and polarized light as a counterclockwise propagating optical signal respectively as a clockwise propagating optical signal and a counterclockwise propagating optical signal through the same optical fiber portion of the optical ring path of the ring interferometer in the same natural linear polarization mode, and propagate a clockwise propagating optical signal and a counterclockwise propagating optical signal through the specimen as orthogonal circularly polarized lights.

A fifty-first aspect of the present invention based on any one of the aspects 41 to 50 (hereinafter referred to as the aspect 51) is the defocused optical rotation measurement method, wherein a mechanism for scanning the specimen orthogonally to the optical path is employed.

A fifty-second aspect of the present invention based on any one of the aspects 41 to 51 (hereinafter referred to as the aspect 52) is the defocused optical rotation measurement method, wherein the specimen is a part of a living body, and the optical rotation measurement method employs, as a detecting means for the optical rotation of the optical signals, means for detecting the phase difference in sync with a technically applied signal for periodically varying dimensions of the part of the living body, such pulse beats of the living body or thickness of a region to be measured, so as to measure optical information on optical rotation of the specimen.

A fifty-third aspect of the present invention based on any one of the aspects 41 to 52 (hereinafter referred to as the aspect 53) is the defocused optical rotation measurement method, wherein the specimen is a part of a living body, the defocused optical rotation measurement apparatus comprises measuring terminals for sandwiching a portion for measuring for optical information on optical rotation of the specimen, and the tip ends of the optical fibers are held by the measuring terminals.

A fifty-fourth aspect of the present invention based on any one of the aspects 41 to 53 (hereinafter referred to as the aspect 54) is the defocused optical rotation measurement method, wherein inter-lens distance adjusting means for changing distance between the output part lens of the one single mode optical fiber and the output part lens of the other single mode optical fiber is employed.

A fifty-fifth aspect of the present invention based on any one of the aspects 41 to 54 (hereinafter referred to as the aspect 55) is the defocused optical rotation measurement method, wherein at least either the one single mode optical fiber or the other single mode optical fiber is a single mode optical fiber connecting via a mode-matching unit a first optical fiber and a second optical fiber differing in core diameter, the first optical fiber is a comparatively smaller core diameter high NA polarization preserving fiber and the second optical fiber is a comparatively larger core diameter low NA polarization preserving fiber, the second optical fiber of the single mode optical fibers is deployed closer to the specimen along the optical path than the first optical fiber, and the output part lens is deployed along the optical path of the optical signal in the vicinity of the end of the second optical fiber closer to the specimen.

A fifty-sixth aspect of the present invention based on any one of the aspects 41 to 55 (hereinafter referred to as the aspect 56) is the defocused optical rotation measurement method, wherein the one optical fiber and the other optical fiber facing each other and sandwiching the specimen along the optical path of the optical signals are the same type of optical fiber.

A fifty-seventh aspect of the present invention based on any one of the aspects 41 to 56 (hereinafter referred to as the aspect 57) is the defocused optical rotation measurement method, wherein the optical fibers facing each other and sandwiching the specimen along the optical path of the optical signals are so-called double-cladding optical fibers.

A fifty-eighth aspect of the present invention based on any one of the aspects 41 to 57 (hereinafter referred to as the aspect 58) is the defocused optical rotation measurement method, wherein at least either an expanded-core fiber or a reduced-core fiber is used in the mode-matching unit.

A fifty-ninth aspect of the present invention based on any one of the aspects 41 to 58 (hereinafter referred to as the aspect 59) is the defocused optical rotation measurement method, wherein distance between the output part lens of the one single mode optical fiber and the output part lens of the other single mode optical fiber is shorter than 3 mm.

A sixtieth aspect of the present invention based on any one of the aspects 41 to 59 (hereinafter referred to as the aspect 60) is the defocused optical rotation measurement method, wherein both of the defocused optical fiber optical systems facing each other and sandwiching the specimen along the optical path of the optical signal and has the polarizer, the Faraday rotary element, the ¼ wave plate, and the output part lenses deployed at the optical fiber ends are on the same side of an optical signal inlet side, and the ¼ wave plate is deployed between the defocused optical fiber optical systems and specimen.

According to a sixty-first aspect of the present invention to solve the problem (hereinafter referred to as the aspect 61), an optical rotation measurement apparatus for measuring for optical information on optical rotation of a specimen by deploying single mode optical fibers, each having a lens deployed at a tip end, along an optical path of an optical signal, facing each other and sandwiching a specimen for optical rotation measurement (referred to as specimen hereafter), such as a light-scattering specimen, irradiating on the specimen an optical signal emitted from an end of one single mode optical fiber having a lens at the tip end, irradiating an optical signal having passed through the specimen or an optical signal reflected by the specimen on an end of the other single mode optical fiber having a lens at the tip end; wherein an optical fiber optical system having a lens (lens deployed at an output part of the optical fibers for an optical signal irradiated on the specimen and/or an inlet part for an optical signal from the specimen is simply referred to as output part lens hereafter) deployed at an output part of the one single mode optical fiber for an optical signal irradiated on the specimen and/or an inlet part for an optical signal from the specimen, and the output part lens deployed at an inlet part of the other single mode optical fiber for an optical signal from the specimen and/or an output part for an optical signal irradiated on the specimen are deployed along the optical path of the optical signal, at least either the one single mode optical fiber or the other single mode optical fiber is a single mode optical fiber connecting via a mode-matching unit a first optical fiber and a second optical fiber differing in core diameter, the first optical fiber is a comparatively smaller core diameter high NA polarization preserving fiber and the second optical fiber is a comparatively larger core diameter low NA polarization preserving fiber, the second optical fiber of the single mode optical fibers is deployed closer to the specimen along the optical path than the first optical fiber, and the output part lens is deployed along the optical path of the optical signal in the vicinity of the end of the second optical fiber closer to the specimen, is used.

A sixty-second aspect of the present invention based on the aspect 61 (hereinafter referred to as the aspect 62) is the optical rotation measurement apparatus, wherein NA of the second optical fiber is 0.07 or less.

A sixty-third aspect of the present invention based on the aspect 61 or 62 (hereinafter referred to as the aspect 63) is the optical rotation measurement apparatus, wherein the optical fiber optical system is a polarized light converting optical system comprising the output part lens, a Faraday rotary element, a ¼ wave plate, and a polarizer along the optical path in the vicinity of an end of the optical fibers.

A sixty-fourth aspect of the present invention based on any one of the aspects 61 to 63 (hereinafter referred to as the aspect 64) is the optical rotation measurement apparatus, wherein the optical rotation measurement apparatus is configured so as to allow measurement of optical rotation of the specimen by constituting an optical ring path for a ring light interference system by the specimen, the defocused optical fiber optical system, and the polarization preserving fibers, and measuring phase difference of the light propagating along the optical path in both directions that occurs due to the specimen.

According to a sixty-fifth aspect of the present invention to solve the problem (hereinafter referred to as the aspect 65), an optical fiber optical system that can employ an optical fiber measuring system for measuring for optical information on optical rotation of a specimen by deploying single mode optical fibers, each having a lens deployed at a tip end, along an optical path of an optical signal, facing each other and sandwiching a specimen for optical rotation measurement (referred to as specimen hereafter), such as a light-scattering specimen, irradiating on the specimen an optical signal emitted from an end of the one single mode optical fiber having a lens at the tip end, irradiating an optical signal having passed through the specimen or an optical signal reflected by the specimen on an end of the other single mode optical fiber having a lens at the tip end; wherein a lens (lens deployed at an output part of the optical fibers for an optical signal irradiated on the specimen and/or an inlet part for an optical signal from the specimen is simply referred to as output part lens hereafter) deployed at an output part of the one single mode optical fiber for an optical signal irradiated on the specimen and/or an inlet part for an optical signal from the specimen, and the output part lens deployed at an inlet part of the other single mode optical fiber for an optical signal from the specimen and/or an output part for an optical signal irradiated on the specimen are deployed along the optical path of the optical signal, at least either the one single mode optical fiber or the other single mode optical fiber is a single mode optical fiber connecting via a mode-matching unit a first optical fiber and a second optical fiber differing in core diameter, the first optical fiber is a comparatively smaller core diameter high NA polarization preserving fiber and the second optical fiber is a comparatively larger core diameter low NA polarization preserving fiber, the second optical fiber of the single mode optical fibers is deployed closer to the specimen along the optical path than the first optical fiber, and the output part lens is deployed along the optical path of the optical signal in the vicinity of the end of the second optical fiber closer to the specimen.

According to a sixty-sixth aspect of the present invention to solve the problem (hereinafter referred to as the aspect 66), a defocused optical rotation measurement method, for measuring for optical information on optical rotation of a specimen by deploying single mode optical fibers, each having a lens deployed at a tip end, along an optical path of an optical signal, facing each other and sandwiching a specimen for optical rotation measurement (referred to as specimen hereafter), such as a light-scattering specimen, irradiating on the specimen an optical signal emitted from an end of the one single mode optical fiber having a lens at the tip end, irradiating an optical signal having passed through the specimen or an optical signal reflected by the specimen on an end of the other single mode optical fiber having a lens at the tip end; wherein a lens (lens deployed at an output part of the optical fibers for an optical signal irradiated on the specimen and/or an inlet part for an optical signal from the specimen is simply referred to as output part lens hereafter) deployed at an output part of the one single mode optical fiber for an optical signal irradiated on the specimen and/or an inlet part for an optical signal from the specimen, and the output part lens deployed at an inlet part of the other single mode optical fiber for an optical signal from the specimen and/or an output part for an optical signal irradiated on the specimen are deployed along the optical path of the optical signal, at least either the one single mode optical fibers or the other single mode optical fiber is a single mode optical fiber connecting via a mode-matching unit a first optical fiber and a second optical fiber differing in core diameter, the first optical fiber is a comparatively smaller core diameter high NA polarization preserving fiber and the second optical fiber is a comparatively larger core diameter low NA polarization preserving fiber, the second optical fiber of the single mode optical fibers is deployed closer to the specimen along the optical path than the first optical fiber, and the output part lens is deployed along the optical path of the optical signal in the vicinity of the end of the second optical fiber closer to the specimen.

Effects of the Invention

According to the defocused optical rotation measurement apparatus of the present invention, or by using the defocused optical fiber optical system and the optical rotation measurement method using the optical fiber optical system, glucose concentration in a living body related to blood sugar level can be measured with high accuracy by measuring small amounts of blood or without drawing any blood.

The present invention achieves great results particularly with a noninvasive measurement method without drawing blood, such that: firstly, the living body is freed from pain during blood collecting; secondly, it is sanitary because blood collecting is not required; thirdly, it is economical since a reagent for reacting with glucose used in the blood drawing method is unnecessary, and therefore the yearly running cost of 100 thousand yen or more is unnecessary; fourthly, blood sugar level can be monitored several times in a day since it is a simple procedure, and it can thus be used for health management of diabetic patients and healthy persons; and fifthly, medical-care expenses paid by the government can also be substantially reduced.

Use of the optical rotation measurement apparatus capable of measuring a light-scattering specimen in the home leads to extremely good news such as drastically decreasing the number of diabetic patients and those with impaired glucose tolerance currently increasing worldwide, and substantial reduction in necessary cost for treatment for the patient. Moreover, use of the optical rotation measurement apparatus and the optical rotation measurement method employing the improved optical fiber optical system including the mode-matching unit according to the present invention allows measurement for optical information on optical rotation of the measured subject with extremely high accuracy that could not

DESCRIPTION OF REFERENCE NUMERALS

Figure 1A:
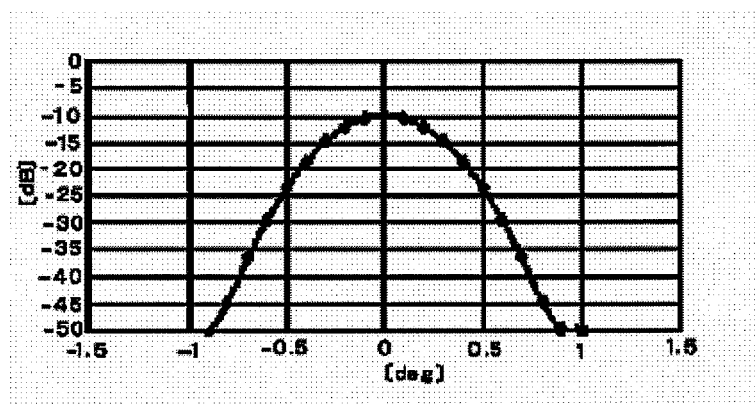
FIGS. 1A and 1B are graphs explaining beam angle dependency (theoretical calculation values) on coupling loss of opposing single mode collimator optical systems that increase initial loss by 10 dB and 20 dB.

1: PM optical fiber constituting a ring
1-1, 1-2, 1-3, 1-4, 1-5, 1-6, 1-7, 1-8: optical fiber
2-1, 2-2: ferrule
3-1, 3-2, 3-3, 35: lens
4, 45: specimen, light-scattering specimen
5-1, 5-2, 37: focal distance
9-1, 9-2, 38: polarizer
11-1, 11-2, 11-3, 39: Faraday rotary element
13-1, 13-2, 13-3, 40, 47: ¼ wave plate
14-1, 14-2: polarized light converting defocused optical system
14-3, 14-4: polarized light converting collimator optical system
15-1, 15-2: PM optical fiber cross-section
16-1, 16-2: incoming light polarizing direction
17, 48: SLD light source
18-1, 18-2: directional coupler
19, 50: optical fiber polarizer
20, 52: optical phase modulator
21, 55: photo detector
22, 56: signal processing circuit
123, 57: phase modulation signal
24: translation stage
25: collimated beam
26-1, 26-2, 26-3: mirror
27-1, 27-2: 45-degree twisted splice
28-1, 28-2: optical fiber polarization beam splitting/combining device
29-1, 29-2, 54-1, 54-2: splice
30: orthogonal polarized wave delay optical circuit
31, 51-1, 51-2: small core diameter high NA polarization preserving fiber
32: large core diameter low NA polarization preserving fiber
32a: optical fiber end
33, 34: mode-matching unit
36: lens focal position
41: polarized light converting collimating optical system including mode-matching unit 42: defocused polarized light converting optical system including mode-matching unit
43: collimated circularly propagating polarized light
44: defocused circularly propagating polarized light
46: glass plate
49-1, 49-2: coupler
53-1, 53-2: clockwise and counterclockwise propagating linearly polarized light
58, 59: optical rotation measurement apparatus
60: visible laser
61: half mirror
62: microscope

DESCRIPTION OF EMBODIMENTS

Embodiments of an aspect of the present invention are explained with reference to drawings hereafter. Note that each drawing used for explanation of the outline of dimensions, form, arrangement, etc. of each constituent element is schematically illustrated to such an extent that the embodiment of the present invention is understandable. For the convenience of description of the present invention, a part of the drawings may be drawn with a different enlargement ratio. Moreover, some drawings used for explanation of an embodiment of the present invention may not be analogous to an actual object and/or description of the embodiment. The same reference numeral is attached to the same constituent elements in each drawing for avoiding redundant explanation. Moreover, in the following description, explanation of a defocused optical rotation measurement apparatus and an optical rotation measurement method using a defocused optical fiber optical system according to the respective embodiments of the present invention include many redundant portions. Therefore, to avoid redundancy of explanation, description of the optical fiber optical system may serve entirely or partially as those of the optical rotation measurement apparatus and the optical rotation measurement method, with keeping those explanations from being misunderstood without particular notice to the effect, or vice versa.

The inventor of the present invention has been expected by many medical experts to implement a measurement apparatus capable of measuring glucose concentration in drawn blood or living bodies with high accuracy and has exerted much effort therein. Reasons thereof have been analyzed extensively in light of the fact that the inventor could not realize this until now.

As a result, the inventor has reached the conclusion that a new measurement principle, which is difficult to implement by the various well-known conventional measurement methods and has not been used in this kind of measuring until now, must be found.

The basic configuration of the measurement apparatus favorably has a ring interferometer using optical fibers, irradiates polarized light on a specimen to be measured, and measures phase change of that polarized light. However, measurement accuracy in particular needs to be improved.

The established theory among specialists is that a ring interferometer sandwiching a specimen between optical fibers performs optical coupling between incoming and outgoing light to/from the specimen using an optical fiber collimator optical system with little optical loss, and is thereby able to reduce insertion loss the most. When measuring intensity change and phase change of an optical signal using the optical fiber collimator optical system, ends of the optical fibers are deployed at the focal positions of the collimator lenses.

Phase change for various specimens has been measured using this method. However, it is understood that as detection accuracy of information on glucide is insufficient for practical application at medical sites, detection accuracy must be further heightened.

Exceeding common practice of these specialists, the inventor of the present invention has constructed the conventional optical fiber polarized light converting optical system (also referred to as conventional polarized light converting optical system hereafter) having optical fiber ends deployed at focal positions of the lenses and the defocused optical fiber polarized light converting optical system (also referred to as defocused polarized light converting optical system hereafter) having optical fiber ends deployed at a distance from the focal positions of the lenses, and has measured phase change of the optical signals for respective specimens in the case where drawn blood or a living body as a specimen is deployed between a pair of conventional polarized light converting optical systems arranged facing each other, and irradiating polarized light as an optical signal on the specimen, and the case where drawn blood or a living body as a specimen with the same conditions as in the case of the conventional polarized light converting optical systems is deployed between a pair of defocused polarized light converting optical systems arranged facing each other, and irradiating polarized light as an optical signal on the specimen.

As a result, it is discovered that the case using the defocused polarized light converting optical systems can measure the phase change of the optical signal with higher accuracy than the case using the conventional polarized light converting optical systems, thereby leading to realization of the present invention.

Figure 1B:
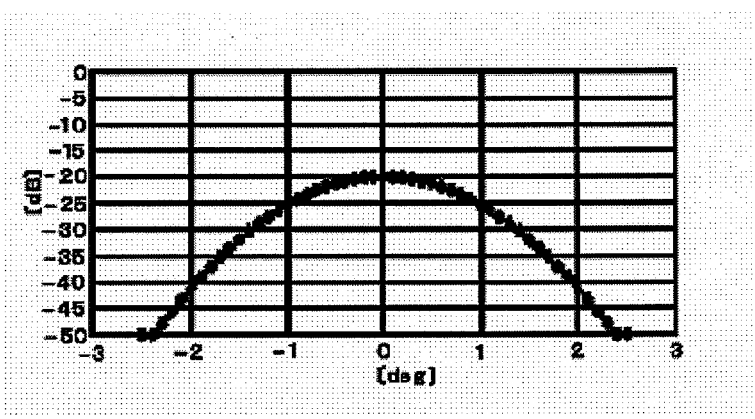

FIG. 1 are examples of results of theoretical calculation by the inventor of the present invention attempting to validate said study results. These are theoretical calculation results of beam angle dependency of opposing single mode optical fiber optical systems using SM optical fibers for a wavelength of 850 nm when focal distance f is 2.5 mm and inter-lens distance is 30 mm. FIG. 1A shows theoretical calculation results of beam angle dependency in the case where an end of an optical fiber is offset (namely, defocused) from the focal point of an output lens, and an initial loss (loss when there is no displacement of beam angle) of 20 dB is provided, and FIG. 1B shows those in the case where an initial loss of 20 dB is provided. In the drawing, the lateral axis gives beam angle of incoming light and the longitudinal axis gives loss (dB). It is understood from the drawing that loss when beam angle is deviated by 0.3 degrees is approximately 5 dB high in the case of an initial loss of 10 dB and is approximately 1 dB in the case of an initial loss of 20 dB. The inventor of the present invention has further studied in detail an actual optical rotation measurement apparatus and optical fiber optical system.

This will be described in further detail while citing embodiments hereafter. An optical rotation measurement apparatus, which is constituted such that it can irradiate an optical signal on a specimen, such as drawn blood or a living body, from an end of one single mode optical fiber having a lens deployed at the tip end, and irradiate an optical signal transmitted through the specimen or an optical signal reflected by the specimen or both the optical signal transmitted through the specimen and the optical signal reflected by the specimen on an end of the other single mode optical fiber having a lens deployed at the tip end, so as to measure for optical information on the optical rotation of the specimen, is employed in embodiments of the present invention.

There are the cases where the one single mode optical fiber and the other single mode optical fiber are different (first embodiment), the one single mode optical fiber and the other single mode optical fiber are the same (second embodiment), the one single mode optical fiber and the other single mode optical fiber are a pair, and there are multiple pairs.

An embodiment of the present invention is characterized in that at least either the one single mode optical fiber or the other single mode optical fiber has an output lens (this output lens is referred to as the output lens irrelevant to that being regarded as a lens for one of the optical signals of the clockwise and the counter clockwise propagating light as an optical signal for the ring interferometer. That is, in the case where it functions as an output side optical fiber for a counter clockwise propagating light, the lens will function as a lens for an input side optical fiber for a clockwise propagating light or the other optical signal) deployed at the tip end, and at least an end of the single mode optical fiber having the output lens constitutes a defocused optical fiber optical system, which is an optical system not deployed at the focal position of the output lens.

Figure 2:
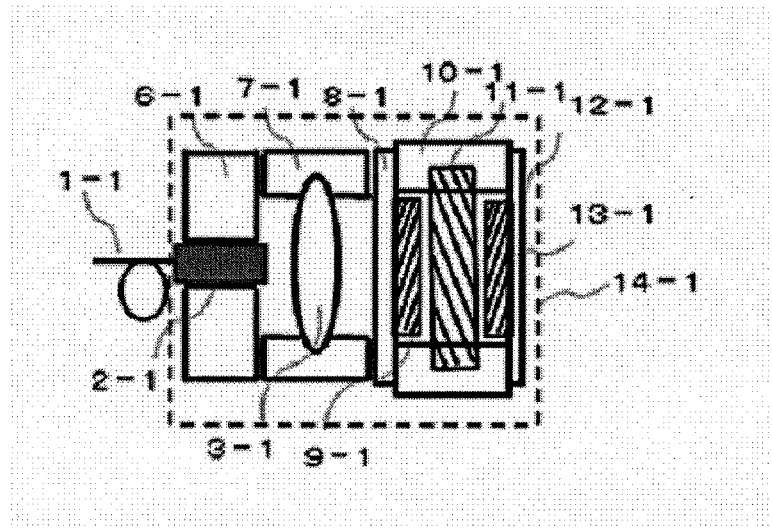
FIG. 2 illustrates a configuration of a defocused polarized light converting optical system as an embodiment of the present invention.
Figure 3:
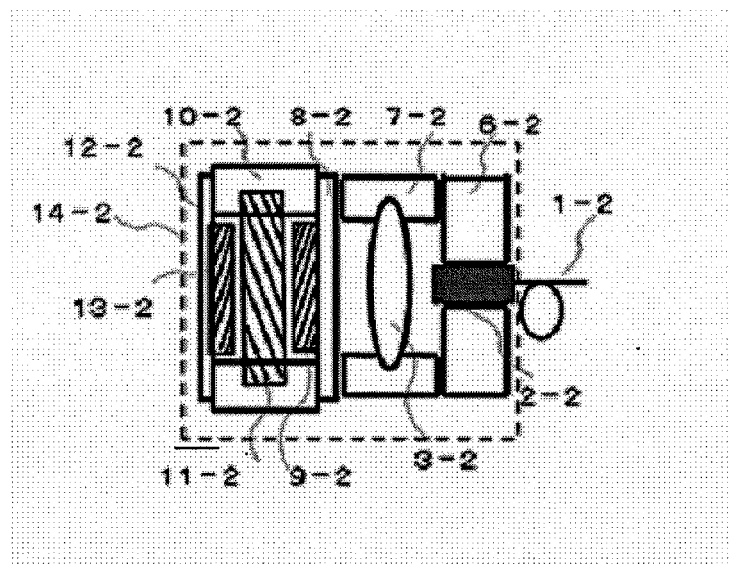
FIG. 3 illustrates a configuration of a defocused polarized light converting optical system as an embodiment of the present invention.

FIG. 2 and FIG. 3 are drawings explaining a configuration of a defocused optical fiber optical system, which is a substantial part of an optical rotation measurement apparatus as an embodiment of the present invention, illustrating a polarized light converting optical system as a defocused optical fiber optical system when a single mode optical fiber is used as a polarization-preserving (PM) optical fiber. With the defocused optical fiber optical system (polarized light converting optical system) of FIG. 2 and FIG. 3, light beams emitted from tip ends of ferrules 2-1 and 2-2 of PM optical fibers 1-1 and 1-2 are guided to an open space via lenses 3-1 and 3-2, polarizers 9-1 and 9-2 held by polarizer holders 8-1 and 8-2, 45-degree Faraday rotary elements 11-1 and 11-2 as the polarization plane rotary elements held by Faraday rotary element holders 10-1 and 10-2, and ¼ wave plates (¼ wavelength plates) 13-1 and 13-2 held by wave plate holders 12-1 and 12-2, respectively, in this order. Reference numerals 14-1 and 14-2 denote defocused polarized light converting optical systems used as opposing systems. The polarized light converting optical systems 14-1 and 14-2 are symmetrical and respectively have a function of converting linearly propagating polarized light emitted from the PM optical fibers to clockwise and counter clockwise propagating polarized lights. In FIG. 2 and FIG. 3, lens focal distance f is 1.8 mm, and distance between lens and optical fiber end is 1 mm, that is, offset from the focal point is 0.8 mm in the direction closer to the lens.

Figure 4:
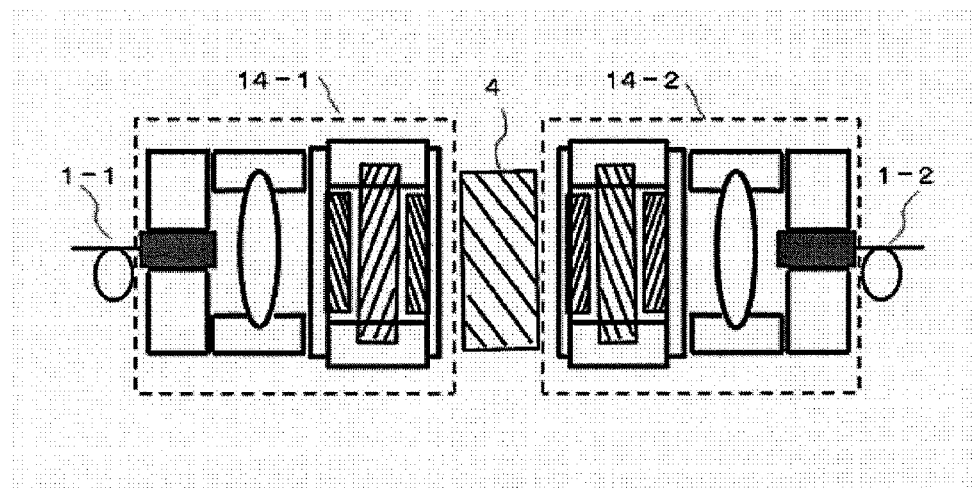
FIG. 4 illustrates a defocused polarized light converting/coupling optical system as an embodiment of the present invention.

FIG. 4 illustrates, as an embodiment of the present invention, a configuration of polarized light converting/coupling optical systems as defocused optical fiber optical systems where polarized light converting optical systems 14-1 and 14-2 are facing each other so as to sandwich a light-scattering specimen 4 as the specimen therebetween. Optical fiber opposing insertion loss is 60 dB. Breakdown thereof is that loss of the (two) Faraday rotary elements is 6 dB and scattering loss in the living body is 54 dB. Note that a light source wavelength of 780 nm is used. This kind of example of sandwiching a part of a living body by opposing single mode optical fibers so as to implement an insertion loss of 54 dB is unprecedented to the best of the inventor's knowledge. This is attained by accommodating three kinds of optical elements: the polarizers 9-1 and 9-2, the Faraday rotary elements 11-1 and 11-2, and the ¼ wave plates 13-1 and 13-2 in a thickness of 0.5 mm, sandwiching the living body so as to be a thickness of 1.5 mm, and keeping the inter-lens distance to 2.5 mm.

Figure 5:
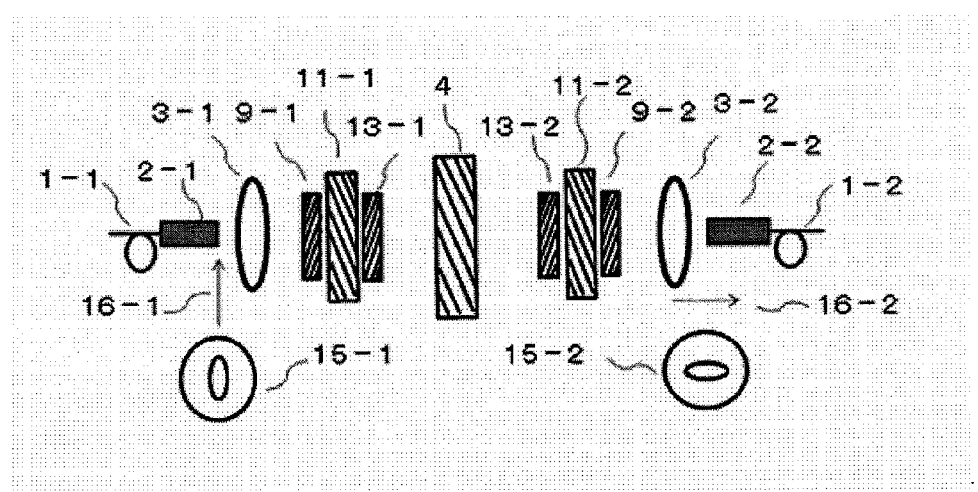
FIG. 5 is a schematic diagram of the principle of a defocused polarized light converting/coupling optical system as an embodiment of the present invention.

FIG. 5 is a schematic diagram of the principle of a defocused polarized light converting/coupling optical system as an optical fiber optical system according to an embodiment of the present invention. Natural polarizing axes of opposing PM optical fibers spatially cross each other, and light emitted from the respective PM optical fibers is in slow axial mode in FIG. 5, but it may be in fast mode. The clockwise propagating polarized light and counterclockwise propagating light are irradiated onto the light-scattering specimen 4 via the 45-degree Faraday rotary elements and the ¼ wave plates of the same specs, thereby coupling the irradiated lights with respective slow axes of the PM optical fibers again. This kind of polarized light converting optical system can be realized using the Faraday rotary elements, which are non-reciprocal elements. Note that while the polarizers 9-1 and 9-2, the Faraday rotary elements 11-1 and 11-2, and the ¼ wave plates 13-1 and 13-2 are deployed between the specimen and the lenses in FIG. 5, they may be deployed between the optical fiber ends and the lenses. As a result, the above light components do not enter between the lenses, thereby allowing smaller inter-lens distance, and low optical fiber facing loss.

Figure 23:
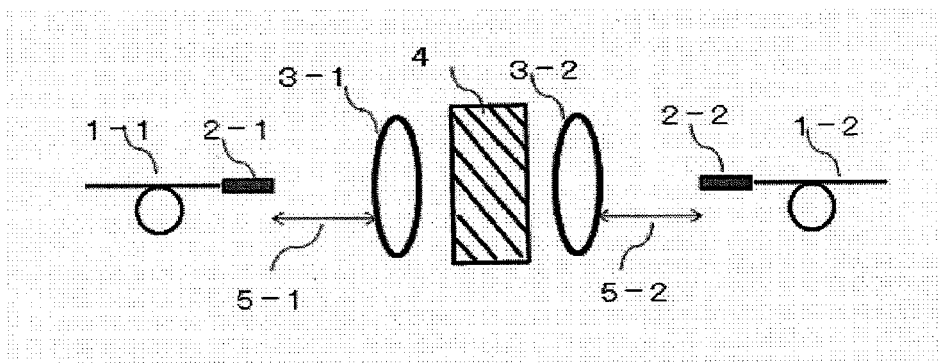
FIG. 23 illustrates a conventional optical system where a light-scattering specimen is inserted between opposing collimators.
Figure 25:
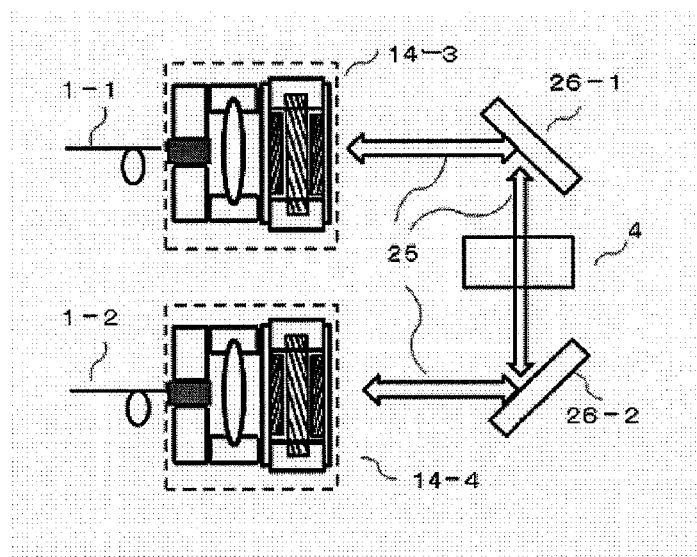
FIG. 25 is a diagram explaining a conventional collimated coupling optical system.

The defocused polarized light converting/coupling optical system of FIG. 5 is used differently from the conventional collimated coupling optical system. FIG. 25 illustrates another conventional collimated coupling optical system. In this case, as in FIG. 23, distances between the lenses and the tip ends of the optical fibers are equal to the focal distances of the respective lenses. Collimated beams 25 emitted from polarized light converting optical systems 14-3 and 14-4 are reflected by mirrors 26-1 and 26-2, respectively. Loss of the coupling system when there is no light-scattering specimen 4 is 1 dB or less, which is small, since it is collimated even if a translation stage 24 is moved to the right side so that the inter-lens distance is several centimeters long. However, when the light-scattering specimen 4 is inserted, coupling loss of the polarized light converting optical systems 14-3 and 14-4 becomes 100 dB or greater, which is very large, and optical rotation cannot be measured.

As a result of various studies as the inventor completes the invention, it is found that in order to keep the insertion loss small in a state where the light-scattering specimen 4 is inserted between opposing polarized light converting/coupling optical systems, positions of the optical fiber tip ends should be shifted from the focal distances of the lenses facing them, namely defocused, instead of using collimated systems as the conventional polarized light converting optical systems 14-3 and 14-4, and scattered light in the living body should be coupled with the opposing single mode optical fibers along the optical path. Conventionally, theoretical examination of such single mode optical fiber opposing systems sandwiching a living body is difficult as light scatters within the living body, and there has not been much theoretical study thereof. Therefore, an experimental study has been conducted.

From experiment, when webbing at the base of the thumb and index finger is sandwiched by polarized light converting/coupling optical systems 14-1 and 14-2 as the defocused optical fiber optical systems of the present invention and optical rotation thereof is measured, coupling loss is smallest in the case of defocusing only 0.8 mm with a lens of a focal distance of 1.8 mm, namely bringing tip ends of optical fibers only 0.8 mm close to the focal position of the lens, and the case of distancing the tip ends of the optical fibers only approximately 0.3 mm from the focal point of a lens with a focal distance of 0.7 mm. About the same level of living body insertion coupling loss is achieved in both cases. These experiment results show that distance between an optical fiber tip end and the opposing lens should be defocused by only approximately half the focal distance of the optical fiber tip end from the focal point of the lens. Note that with the present invention, in the case where the specimen is a part of a living body, such as a webbing portion at the base of the thumb and index finger, making tip ends of the optical fiber optical system of the present invention be a sandwiching structure like forceps and controlling conditions of sandwiching the living body may further heighten measurement accuracy.

Figure 6:
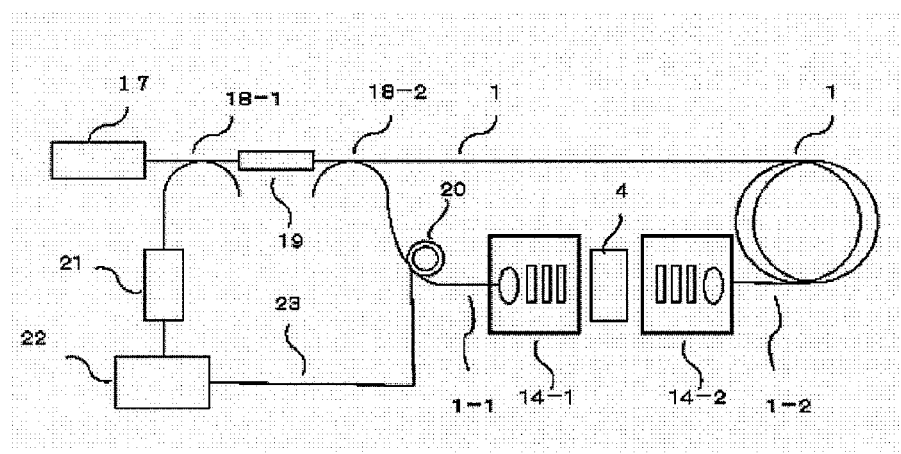
FIG. 6 illustrates a configuration of a defocused optical rotation measurement apparatus as an embodiment of the present invention.

FIG. 6 illustrates a configuration of an optical rotation measurement apparatus for a living body in which a polarized light converting/coupling optical system is used as a defocused optical fiber optical system according to an embodiment of the present invention in a ring light interference system A light source 17 is a super luminescent diode (SLD) of wavelength 780 nm, and output thereof is lead to a first directional coupler 18-1, an optical fiber polarizer 19, and a second directional coupler 18-2, divided into a PM optical fiber 1, which constitutes a ring, and a PM optical fiber 1-1, thereby generating clockwise and counterclockwise propagating lights. Reference numeral 20 denotes an optical phase modulator with an approximately 1 m-long PM optical fiber wrapped around cylinder-type PZT (lead zirconate titanate). The clockwise and the counter-clockwise propagating light revolving through the ring runs through the second and the first directional coupler again and are then converted to electrical signals by a photo detector 21, so as for a signal processing circuit 22 to calculate phase difference of the clockwise and the counter-clockwise propagating light from the optical rotation of the light-scattering specimen 4. A 20 KHz modulated sinusoidal signal is applied to the optical phase modulator 20 from the signal processing circuit 22.

Signal processing in FIG. 6 employs a method using a phase modulating system optical fiber gyro described in Non-patent Document 2. Modulating the phase by 20 KHz allows the ring light interference system to output a 20 KHz fundamental frequency, a 40 KHz second frequency component, and an 80 KHz fourth frequency component. Phase difference between the clockwise and the counter-clockwise propagating light, which have propagated through the optical ring path, is found from a ratio of the fundamental frequency to the second frequency. A ratio of the second frequency to the fourth frequency is proportional to degree of phase modulation, and is thus controlled to be constant.

In FIG. 6, the optical ring path of the ring light interference system is constituted by the PM optical fiber 1 constituting a loop and the polarized light converting optical systems 14-1 and 14-2 as the defocused optical fiber optical systems according to an embodiment of the present invention. A highly important point in FIG. 6 is that the clockwise and counter-clockwise propagating lights propagate as clockwise and counter-clockwise propagating polarized light, respectively, only through the inside of the light-scattering specimen 4, and propagate through the remaining portions of the PM optical fibers in the slow axial polarization mode of the same PM optical fibers. This allows stable measurement of only the phase difference of the clockwise and counter-clockwise propagating polarized lights in the light-scattering specimen. Generally, linearly polarized light is broken down into clockwise and counter-clockwise propagating polarized lights, and when phase difference of $2\theta$ therebetween occurs, direction of the polarized light changes by only $\theta$. In FIG. 6, since phase difference between the clockwise and the counter-clockwise propagating polarized light in the light-scattering specimen is possible, measurement of optic rotation is possible.

To begin with, optic rotation in 1 mm-thick whole blood is measured using the polarized light converting/coupling optical system as the defocused optical fiber optical system of FIG. 4. In this experiment, f is 1.8 mm and offset between fiber and lens is 0.9 mm. That is, distance between the lenses of the polarized light converting optical systems 14-1 and 14-2 and the tip ends of the ferrules 2-1 and 2-2 respectively is fixed at 0.9 mm. The levels of loss of the optical interference systems in this experiment are as given below.

Light source output: 10 mW (PM optical fiber output)
Optical gyro (ring interference system) loss: 10 dB
Insertion loss of defocused polarized light converting/coupling optical systems sandwiching blood: 40 dB
Connector and splice loss: 3 dB
Total loss: 53 dB
Light receiving power: 50 nW In this case, a photo detector uses a silicon APD having a minimum reception sensitivity of 5 pW at a bandwidth of 100 KHz. Under such conditions, phase difference of 0.001 degrees of the clockwise and counterclockwise propagating polarized light transmitting through the whole blood in an average measurement time of 10 seconds can be measured from a sufficient signal-to-noise ratio. That is, if it is converted to glucose concentration, it can be measured at a noise width equivalent to 10 mg/dl. In addition, a reference phase for the clockwise and the counter-clockwise propagating polarized light is a measured value of the case where the specimen is purified water. Note that since the beam diameter is approximately 0.1 mm, quantity of blood required for measurement needs to be only several μ liters, which is an extremely small amount.

Next, webbing at the base of the thumb and index finger is measured as the light-scattering specimen. In this experiment, a light source of an output of 1060 nm and SLD of 50 mW is used. Similarly, f is 1.8 mm and the offset from the lens focal points of the optical fiber tip ends is 0.9 mm. That is, distance between the lenses of the polarized light converting optical systems 14-1 and 14-2 and the tip ends of the ferrules 2-1 and 2-2 respectively is fixed at 0.9 mm.

The levels of loss in the optical interference systems in this experiment are as given below.

Light source power: 50 mW (PM optical fiber output)
Optical gyro ((ring interference system) loss: 10 dB
Insertion loss of defocused polarized light converting/coupling optical systems sandwiching blood: 55 dB
(Note that at a wavelength of 1060 nm, loss of the Faraday rotary element is less than at 780 nm.)
Connector and splice loss: 5 dB
Total loss: 70 dB
Light receiving power: 5 nW In this case as well, a silicon APD having a minimum reception sensitivity of 5 pW at a bandwidth of 100 KHz is used as a photo detector. S/N of the light receiving system is approximately 30 dB.

In this experiment, a refractive index matching material is applied to the webbing of the fingers so as to control reflection loss. Signals in sync with pulse beats are detected in this experiment. Phase difference is measured while shifting the measured region in a perpendicular direction to the optical axis. Phase difference varies according to region as a result. This is interpreted as resulting from difference in cases of the beam propagating and not propagating through a blood vessel. Data on blood sugar can be obtained by repeating measurement of actual diabetic patients. Note that aside from detecting signals in sync with pulse beats, a method of applying periodical pressure on the sandwiching portion of the living body so as to periodically change the thickness of the living body, and detect periodical signals in sync with those periods is also considered effective.

The light source wavelengths in the above embodiment are set to 780 nm and 1060 nm, however, the 1550 nm band may be used. In this case, loss of the Faraday rotary element is smaller than in the case of 780 nm, and absorption loss of water when the light-scattering specimen is a living body is larger. Moreover, the 1060 nm band is the wavelength band for fiber laser, and has merits that light of 100 mW or greater can be easily applied as the light source power, and the core diameter is 20 to 30 μm, practically applying a dramatically larger PM optical fiber than the conventional PM optical fiber.

Figure 7:
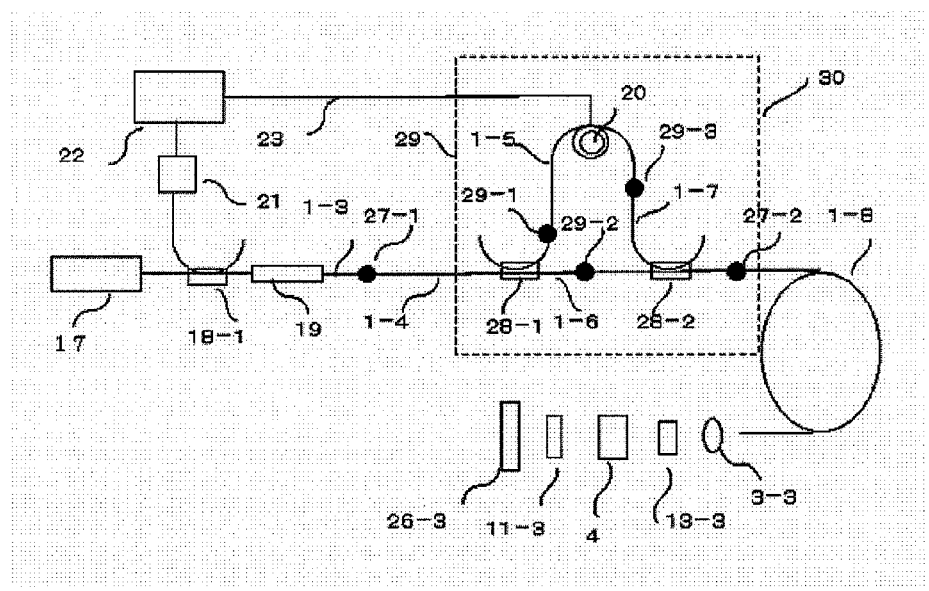
FIG. 7 illustrates a configuration of a defocused optical rotation measurement apparatus as an embodiment of the present invention.

FIG. 7 illustrates a configuration of an optical rotation measurement apparatus for a living body in the case where a polarized light converting optical system as a defocused optical fiber optical system, which is a modification of the previous embodiment of the present invention, is used in a reflecting optical interference system. A light source 17 is a 780 nm SLD, and output thereof is led to an optical fiber polarization beam splitting/combining device 28-1 via the first directional coupler 18-1, the optical fiber polarizer 19, a 45-degree twisted splice 27-1, and a PM optical fiber 1-4. A natural orthogonally polarized mode split by the optical fiber polarization beam splitting/combining device 28-1 is led to a second optical fiber polarization beam splitting/combining device 28-2 via PM optical fibers 1-5, 1-7, and 1-6. Reference numerals 29-1, 29-2, and 29-3 denote splices. Reference numeral 20 denotes an optical phase modulator with an approximately 1 m-long PM optical fiber wrapped around cylinder-type PZT. The sum of the lengths of the PM optical fibers 1-5 and 1-7 is 100 m. Reference numeral 30 denotes a delay optical system, which includes an optical fiber polarization beam splitting/combining device and an optical phase modulator and generates difference in propagation time between two orthogonally polarized modes.

The optical fiber polarization beam splitting/combining device 28-2 is led to a PM optical fiber 1-8 via a second 45-degree twisted splice 27-2, and the two orthogonally polarized modes propagate through the PM optical fiber 1-8 and led to a lens 3-3. Orientation of a Faraday rotary element 11-3 and a ¼ wave plate 13-3 can be set such that two natural polarized components of equal amplitude emitted from the PM optical fiber 1-8 transmit through the lens 3-3 and the ¼ wave plate 13-3, clockwise and counterclockwise propagating polarized lights enter the light-scattering specimen 4, the lights having propagated the light-scattering specimen 4 transmit through the Faraday rotary element 11-3 and reflect off of a mirror 26-3 and propagate through the light-scattering specimen again in the reverse direction and transmit through the ¼ wave plate 13-3 and the lens 3-3 and then couples to the PM optical fiber 1-8 in the natural polarization mode orthogonal to the output polarized light.

A characteristic of such reflecting optical rotation measurement apparatus is a merit that the Faraday rotary element and the ¼ wave plate can be unitary unlike the ring interference-type optical rotation measurement apparatus of FIG. 6. In FIG. 7, since the orthogonally polarized modes propagating through the PM optical fiber 1-8 cross each other when going and returning, phase difference does not occur in the PM optical fiber 1-8. Moreover, since the delay optical system 30 allows the orthogonally polarized modes to propagate through the PM optical fibers 1-5 and 1-7 one time each two ways in the same manner, the orthogonally polarized mode split by the optical fiber polarization beam splitting/combining device 28-1 returns in the same phase within the optical fiber transmission portion. In other words, only phase difference can be measured from the optical rotation of the light-scattering specimen 4 at the defocused polarized light converting optical system of the tip end of the PM optical fiber 1-8. The method of measuring the phase difference of the orthogonally polarized modes that have returned to the photo detector 21 via the optical fiber polarization beam splitting/combining device 28-1, the polarizer 19, and the directional coupler 18-1 is the same phase modulating system as the detecting system of FIG. 6.

In order to make an outgoing light from the single mode optical fiber enter the light-scattering specimen, such as blood or a living body, and the transmitted light from the light-scattering specimen couple with opposing single mode optical fibers efficiently, a mechanism capable of controlling inter-lens distance is provided allowing further increase in optical rotation measuring accuracy according to the present invention.

Furthermore, in an embodiment of the present invention, a mechanism of scanning a specimen in an orthogonal direction to an optical path of an optical signal is provided so as to find areas with good detection sensitivity and select a position for measurement, thereby allowing higher measurement accuracy and improvement in usability.

Figure 8:
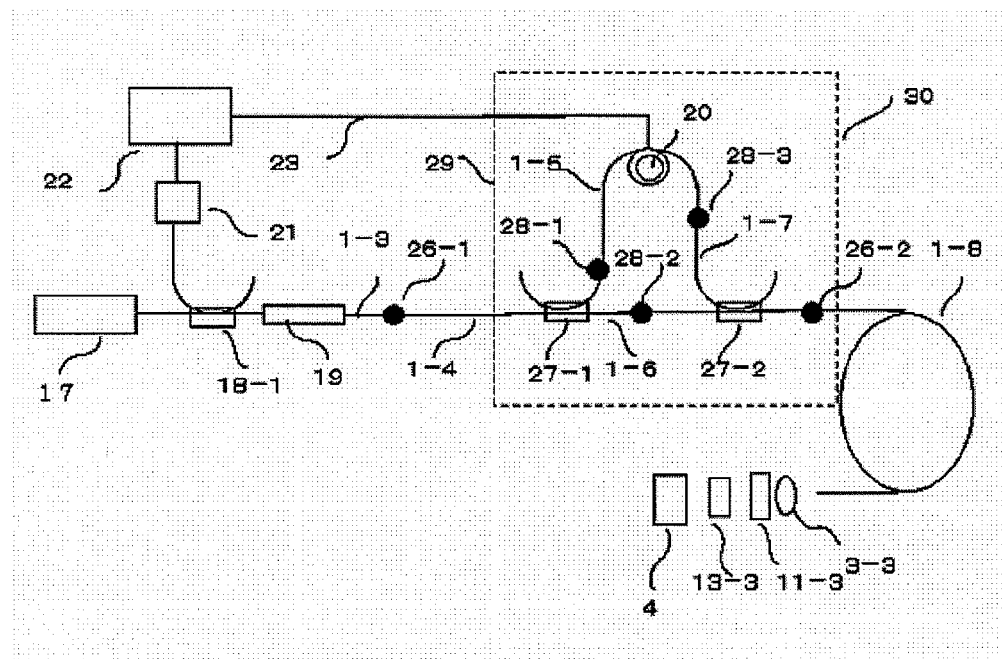
FIG. 8 illustrates a configuration of a defocused optical rotation measurement apparatus as an embodiment of the present invention.

FIG. 8 illustrates a configuration of an optical rotation measurement apparatus for a living body in the case where a polarized light converting optical system as a defocused optical fiber optical system of the present invention is used in a reflecting optical interference system, as an embodiment of the present invention. The difference between FIG. 8 and FIG. 7 is that a mirror is not used behind the light-scattering specimen in FIG. 8. That is, in FIG. 8, the reflected light from the light-scattering specimen 4 is re-coupled with the PM optical fiber 1-8 via the ¼ wave plate 13-3 and the Faraday rotary element 11-3. Generally, since if the clockwise propagating polarized light is reflected by the light-scattering specimen, it returns as a clockwise propagating polarized light, and therefore optical rotation cannot be measured with the optical system of FIG. 8, theoretically. However, there are cases where phase difference between clockwise and counterclockwise propagating polarized lights two ways is not always compensated in random scattering in a living body or the like, and sensitivity is decreased, yet measurement is possible. While thickness of the light-scattering specimen is controlled and measuring region is limited with the measuring system of FIG. 7, a sensor needs to only make contact with the measuring subject with the measuring system of FIG. 8, and thus has a merit that the constitution of the sensor is very simple.

According to the technical ideas of the present invention, the optical fiber optical systems having lenses deployed at the tip ends used in the optical rotation measurement apparatus, the optical fiber optical system, and the optical rotation measurement method of the present invention employ optical fiber optical systems having end faces of the optical fibers not deployed at focal positions of the lenses.

Figure 24:
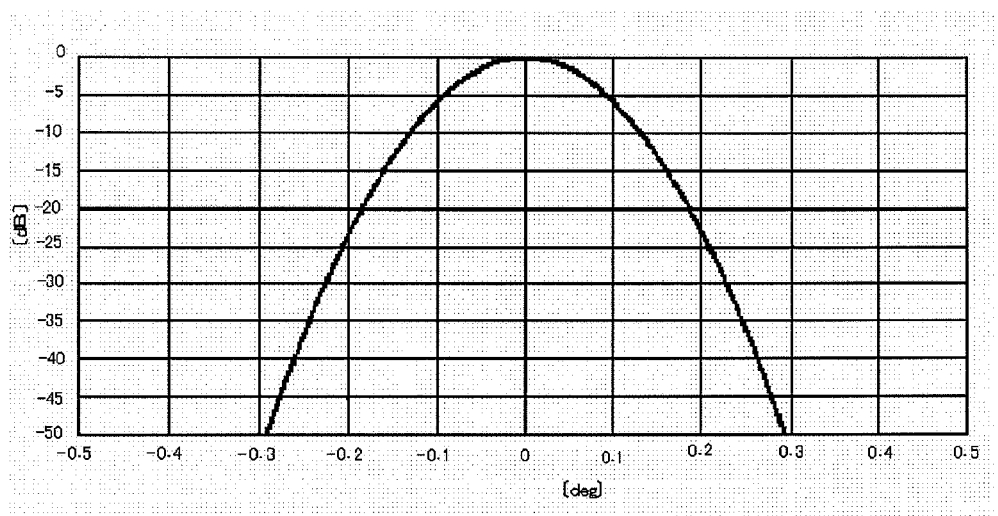
FIG. 24 is a graph explaining beam angle dependency (theoretical calculation values) on coupling loss of the opposing single mode optical systems.

As is well known, in the case where single mode optical fibers respectively having a lens at the tip end are facing each other, and are optically coupled from one to the other, coupling loss will be highest when the ends of the respective optical fibers are deployed at the focal positions of the lenses so as to optically couple by constituting opposing collimators. However, increase in coupling loss for change in incident angle or emitting angle of the optical fibers increases, for example, coupling loss increases 50 dB or greater when the beam angle shifts approximately 0.3 degrees, as explained using FIG. 24. This loss increase is unacceptable in the case of the measuring subject according to the present invention.

As described above, the inventor of the present invention has found that, as a result of various studies, while loss in the case where there is no shift in incident and emitting angles increases a little due to shifting and deploying optical fiber ends from the focal positions of the lenses, angular dependency of beams can be substantially alleviated. With that, coupling loss of opposing optical fibers in the direction (positive direction) of moving the lenses closer to the positions of the optical fiber ends from the focal positions of the lenses and the direction (negative direction) away from the lenses is examined through experiment.

For example, when paired, 1550 nm PM optical fibers, each having a lens with a focal distance of 0.7 mm deployed at an end face of one of the fibers, face each other where a lens opposing distance is 2 mm and distance (offset) between the focal point and one of the fiber ends is set to +400 to +1000 µm, loss is 68 dB, which is large. If the lens opposing distance is 3 mm, loss is 80 dB or greater for any offset.

If the lens opposing distance is 2 mm when the lens focal distance is 2.75 mm, loss is 70 dB with an offset of −250 to +1200 µm.

When the lens opposing distance is 2 mm in the case of focal distance of 1.8 mm, loss is 65 dB with an offset of −250 to +1200 µm. However, if the inter-lens distance is 1.5 mm and the offset is −800 µm, loss can be 52 dB, and loss in a state where the optical fiber end makes contact with the lens can be 49 dB. In this case, the optical fiber end can be brought into contact with the lens, and a polarizer, a Faraday rotary element, and a ¼ wave plate (the ¼ wave plate is unnecessary when a linearly polarized light is used instead of a circularly propagating polarized light) can be deployed on the outside (opposite side than side where the optical fiber end is deployed) of the lens.

Moreover, even if the opposing distance is 2 mm and inter-lens distance that achieves a minimum loss of 35.3 dB is approximately 3 mm when using a double-cladding optical fiber, which is a 1060 nm PM optical fiber for a fiber laser having a core diameter of 30 µm, there is little increase in loss. This is a significant improvement as compared to the insertion loss of the defocused polarized light converting/coupling optical system described above. The inventor has also tested using multimode optical fibers with a core diameter of 62.6 µm in the defocused polarized light converting/coupling optical system for comparison. However, an insertion loss of 45 dB or less has not been achieved, and loss has exponentially increased when the inter-lens distance is approximately 3 mm.

It is found from results of these many experiments that deploying the optical fiber end at a position near the lens from the focal point or a position away from the lens instead of deploying at the lens focal point is preferable for reducing coupling loss of optical signals. In particular, it is further preferable to bring the optical fiber end as close to the lens as possible when using lens with a focal distance of 0.7 to 2.75 mm. Mounting the polarizer, the Faraday rotary element, and the ¼ wave plate between the lenses and the optical fiber ends with intervals of 0.6 mm or less, and measuring optical rotation in the studying process of the above embodiment has allowed measurement of optical rotation with high accuracy.

Moreover, with the opposing optical fiber optical system where at least two of the defocused optical fiber optical systems according to the present invention face each other, sandwiching a specimen in the optical path of optical signals, if inter-opposing lens distance is made greater than 4 mm, insertion loss when the specimen is a living body increases. Suppressing the inter-opposing lens distance to 4 mm or less allows insertion loss measured in the same manner as in the previous embodiment to be 50 dB or less, and increase in measurement accuracy of optical information on optical rotation. Further preferable is that by making the inter-opposing lens distance be less than 3 mm, the insertion loss measured in the same manner as in the previous embodiment can be 45 dB or less, and measurement accuracy of optical information on optical rotation can be further heightened.

In addition, with the defocused optical rotation measurement apparatus, the defocused optical fiber optical system, and the optical rotation measurement method using that optical system according to the present invention, fixation of tip ends of the optical fibers and the lenses, which are user friendly, allows measurement of optical information on optical rotation, which is easily reproducible, with high accuracy.

Deploying the optical fiber ends and the output lenses in a defocused state and measuring optical information on optical rotation of a specimen with high accuracy that could never be achieved conventionally has been explained in the embodiments of the present invention while referencing the drawings.

Next, improvement allowing measurement of optical information on optical rotation of a specimen with extremely high accuracy through improvement of the polarization preserving fiber will be explained.

The inventor examined through experiment insertion loss when the core diameter of the polarization preserving fiber used in an opposing defocused polarized light converting optical system is changed variously and inserted into the opposing defocused polarized light converting optical system. As a result, it is found that if a large core diameter low NA (NA denotes numerical aperture) polarization preserving fiber having a core diameter of 20 to 30 µm for wavelength 1064 nm, which is currently used for optical fiber lasers, insertion loss can be lower by 20 to 30 dB than when a polarization preserving fiber having a core diameter of 10 µm is used.

A reason that the insertion loss has decreased substantially lower than the normal PM 980 (core diameter is approximately 7 µm, and NA is approximately 0.2) in the case of using a double-cladding optical fiber for a fiber laser having a core diameter of 30 µm and thereby NA of approximately 0.07 as the polarization preserving fiber used in the opposing defocused polarized light converting optical systems under defocused conditions is that since the NA is small, the sample can be irradiated at a small angle without concentration of light at the lens, thereby keeping scattering loss lower. Another considered reason is that a mode in which light scattered by the light-scattering specimen is all reflected by a second clad of the double-cladding optical fiber is coupled with the single mode of the 30 µm core.

At the same time, since a specimen is placed in the optical ring path of the ring interferometer during optical rotation measurement according to the present invention, an optical fiber-type coupler, namely a 2×2 directional coupler for branching light from a light source into clockwise propagating light and counterclockwise propagating light and then coupling them is required. However, a coupler for a polarization preserving fiber having a 20 to 30 µm core diameter is not commercially available. Moreover, there is a problem that while a rather long ring fiber is required when employing a so-called phase modulating system for optical rotation measurement according to the present invention, the polarization preserving fiber having a 20 to 30 µm core diameter is expensive, and is therefore not economical.

Figure 9:
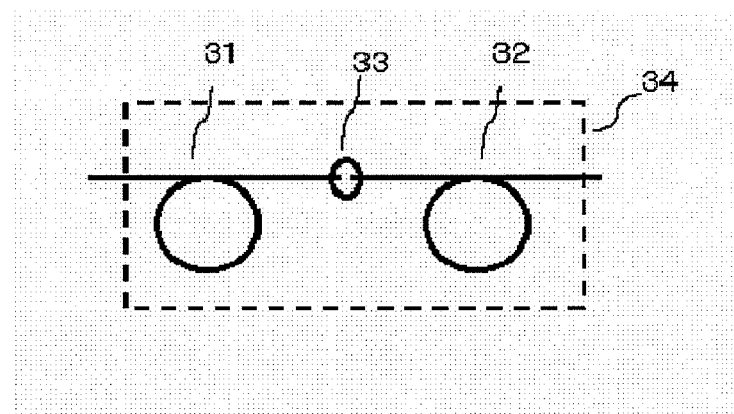
FIG. 9 is a diagram explaining a mode-matching unit used in the embodiments of the present invention.
Figure 10:
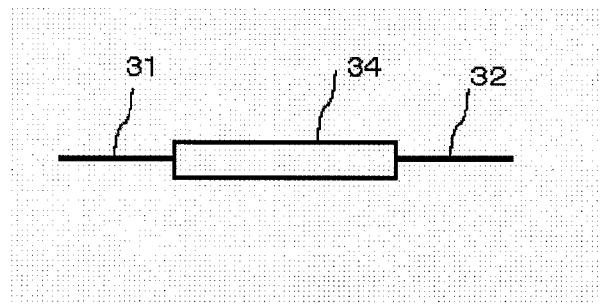
FIG. 10 is a diagram explaining a mode-matching unit used in the embodiments of the present invention.

Because of this situation, the inventor has designed to match modes of conventional polarization preserving fibers having core diameters of 10 µm and 30 µm. FIG. 9 is a diagram explaining a mode-matching unit used in the embodiments of the present invention. That is, the vicinity of an emitting part or end of a relatively small core diameter high NA polarization preserving fiber 31 as a first optical fiber is heated, so as to enlarge the core part, that is, to make it into a so-called expanded-core optical fiber. Afterwards, the end of the small core diameter high NA polarization preserving fiber 31 as the first optical fiber, which became the expanded-core optical fiber is connected to the end of a large core diameter low NA polarization preserving fiber 32 as a second optical fiber via a mode-matching unit 33, so as to reinforce the connection. While coupling loss is approximately 3 dB, loss can be further reduced if heating conditions are optimized. FIG. 10 is a diagram explaining a mode-matching unit 34 used in the embodiments of the present invention. The mode-matching unit 33 and the mode-matching unit 34 make a structure including at least an end portion constituting the expanded-core optical fiber of the first optical fiber and an end portion of the second optical fiber connected thereto; however, many variations are possible without being limited narrowly thereto. As an example, the end of the second optical fiber on the side connected to the first optical fiber may be heated near the end of the second optical fiber and lengthened, forming it such that the core diameter near the end of the second optical fiber tapers toward the side connected to the first optical fiber, and connected to the first optical fiber. Moreover, since an expanded-core portion or a reduced-core portion often deforms in some degree by heat during processing of the outer shape of the optical fiber, coupling loss due to a processing error developed through processing the end portion of the first optical fiber into an expanded-core fiber, processing the end portion of the second optical fiber into a reduced-core fiber, and connecting both of the end portions.

Figure 11:
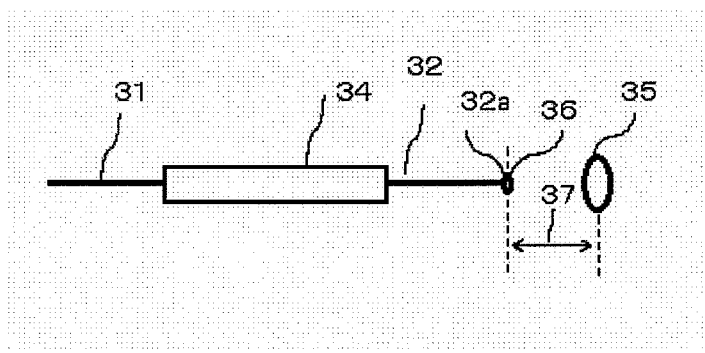
FIG. 11 is a diagram explaining how to create collimated light from the mode-matching unit used in the embodiments of the present invention.
Figure 12:
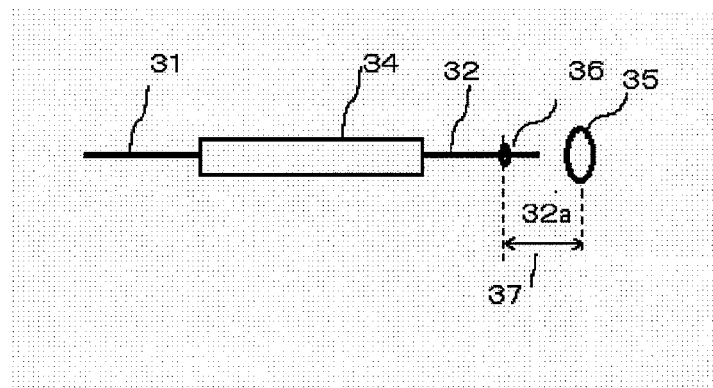
FIG. 12 is a diagram explaining how to create defocused light from the mode-matching unit used in the embodiments of the present invention.

While the embodiment in which the end of the small core diameter high NA polarization preserving fiber 31 as the first optical fiber and the end of a large core diameter low NA polarization preserving fiber 32 as the second optical fiber, which are a part of the fundamental technical ideas of the present invention described below, are connected via the mode-matching unit 33 and used achieves great results even with a collimating propagated light converting optical system. FIG. 11 is a diagram explaining how the mode-matching unit used in the embodiments of the present invention creates collimated light. That is, an end 32a of an optical fiber 32 is deployed at a focal position 36 of a lens 35. Note that an arrow given reference numeral 37 in FIGS. 11 to 14 denotes focal distance of the lens 35. FIG. 12 is a diagram explaining how the mode-matching unit used in embodiments of the present invention creates defocused light. In this case, the end 32a of the optical fiber 32 is deployed further on the lens side than the focal position 36.

An optical rotation measurement apparatus, a propagated light converting optical system, and an optical rotation measurement method according to an embodiment of the present invention use an optical ring path of a ring interferometer; a specimen is deployed in the optical ring path; an optical fiber terminal along the optical ring path and another optical fiber terminal along the optical ring path, which face each other and sandwich the specimen in an optical path of an optical signal, respectively comprise a polarized light converting optical system; and the polarized light converting optical systems constitute a non-reciprocal optical system using a polarization plane rotary element. It is preferable to employ as the polarization plane rotary element, a polarization plane rotary element, which acts so as to rotate a polarization plane of an optical signal clockwise or counterclockwise only a predetermined angle in the traveling direction of the optical signal when a polarized light beam enters as the optical signal from one side of the polarization plane rotary element, and otherwise to rotate a polarization plane of the optical signal clockwise or counterclockwise in the traveling direction of the optical signal, namely rotate only a predetermined angle in the same direction as in the case of an optical signal that enters from the one side when a polarized light beam enters as the optical signal from the other side of the polarization plane rotary element when viewed in the direction of the progressing optical signal that has entered from the one side. With the optical rotation measurement apparatus according to the embodiments of the present invention, polarized light as a clockwise propagating optical signal and polarized light as a counterclockwise propagating optical signal are propagated through the optical ring path of the ring interferometer, and as described below, the polarized light of the clockwise propagating optical signal and the polarized light as the counterclockwise propagating optical signal are propagated through the same optical fiber portion in the optical ring path of the ring interferometer in the same natural polarization mode, and the specimen portion allows the signals to propagate as a clockwise and a counter-clockwise propagating optical signal, respectively, in the forms of mutually crossing circularly polarized lights, thereby allowing detection of optical rotation of the specimen with high accuracy utilizing the respective configurations of the present invention.

The aforementioned embodiment is an example using the same element as the two polarization plane rotary elements, and it is the case where natural polarizing axes of the two optical fiber terminals, which face each other sandwiching the specimen on the optical path, cross each other along the optical ring path. While the optical rotation measurement apparatus, the propagated light converting optical system, and the optical rotation measurement method of the present invention can be implemented even if the natural polarizing axes of the two optical fiber terminals, which face each other sandwiching the specimen on the optical path, are parallel, in order to achieve the same results as the aforementioned embodiment of the present invention, the polarization plane rotative directions of the two polarization plane rotary elements need to be in the same direction of the traveling optical signals. However, two types of the polarization plane rotary element that have an opposite rotative direction are required in this case.

The polarization plane rotary element described using a Faraday rotary element according to the embodiments of the present invention is a non-reciprocal optical system and its action is as described above. The Faraday rotary element here is one that makes a polarization plane rotate 45 degrees in a predetermined direction.

Figure 13:
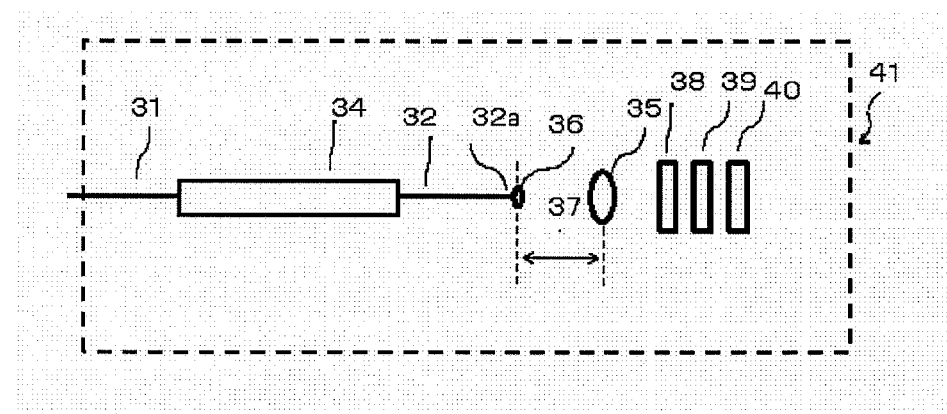
FIG. 13 is a diagram illustrating how to create collimated circularly propagating polarized light from the mode-matching unit used in the embodiments of the present invention.
Figure 14:
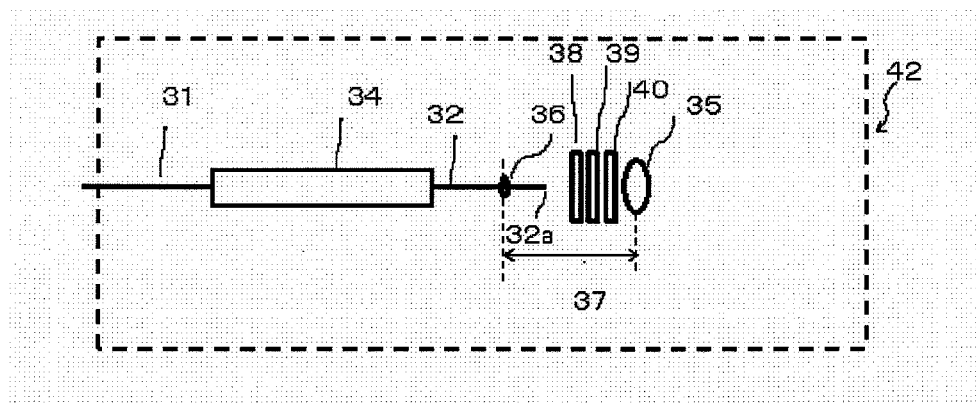
FIG. 14 is a diagram illustrating how to create defocused circularly propagating polarized light from the mode-matching unit used in the embodiments of the present invention.

FIG. 13 is a diagram illustrating how the mode-matching unit used in the embodiments of the present invention creates collimated circularly propagating polarized light. The end 32a of the optical fiber 32 is deployed at the focal position 36 of the lens 35 in FIG. 13. Reference numeral 41 in FIG. 13 denotes a polarized light converting/collimator optical system including the mode-matching unit. FIG. 14 is a diagram illustrating how the mode-matching unit used in the embodiments of the present invention creates defocused circularly propagating polarized light. The end 32a of the optical fiber 32 is deployed further on the lens side than the focal position 36 of the lens 35 in FIG. 14. In FIG. 13, a linearly polarized emitted light of the large core diameter low NA polarization preserving fiber 32, which is a pigtail of the mode-matching unit 34, is collimated as an optical signal by the lens 35, and is made into a circularly-propagating polarized light via a polarizer 38, a Faraday rotary element 39, and a ¼ wave plate 40 in this order. Reference numeral 42 in FIG. 14 denotes a defocused polarized light converting optical system including the mode-matching unit. The polarizer 38, the Faraday rotary element 39, and the ¼ wave plate 40 are deployed between the lens 35 and the end 32a of the optical fiber 32; however, they may be deployed behind the lens 35 as in the case of the collimating optical system of FIG. 13, namely on the opposite side of the lens 35 than the end 32a of the optical fiber 32.

Figure 15:
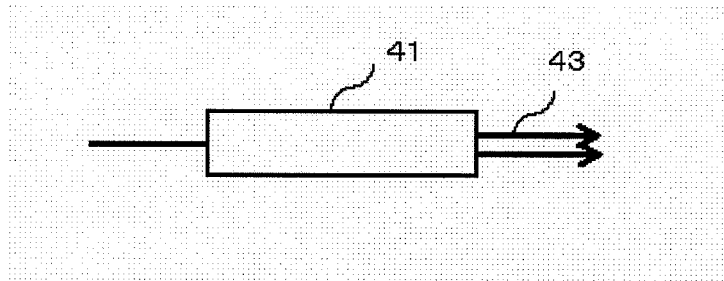
FIG. 15 is a diagram conceptually illustrating beams emitted from a circularly propagating polarized light converting collimator that includes the mode-matching unit used in the embodiments of the present invention.
Figure 16:
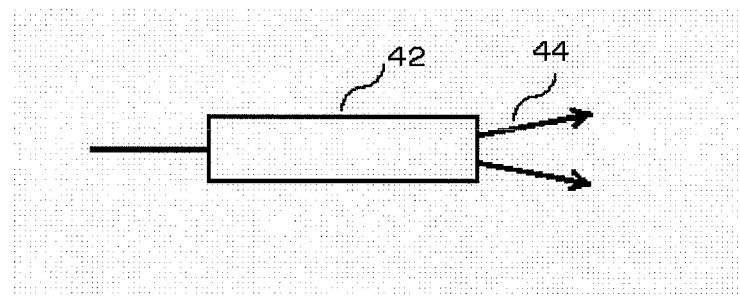
FIG. 16 is a diagram conceptually illustrating beams emitted from a circularly propagating polarized light/defocused polarized light converting optical system that includes the mode-matching unit used in the embodiments of the present invention.

FIG. 15 is a diagram conceptually illustrating beams emitted from a circularly propagating polarized light converting collimator that includes the mode-matching unit used in the embodiments of the present invention. FIG. 16 is a diagram conceptually illustrating beams emitted from a circularly propagating polarization/defocused optical system that includes the mode-matching unit used in the embodiments of the present invention.

In FIG. 15, beams 43 emitted from a circularly propagating polarized light converting collimator 41 including the mode-matching unit (mode-matching/polarized light converting collimator) are collimated circularly propagating polarized lights, which are collimated beams, and are irradiated onto a specimen (omitted from the drawing) that is deployed in the traveling direction of the lights. In FIG. 16, beams 44 emitted from a defocused polarized light converting collimator 42 including the mode-matching unit (mode-matching/defocused polarized light converting optical system) are defocused circularly propagating polarized lights, which are diverging beams, and are irradiated onto a specimen (omitted from the drawing) that is deployed in the traveling direction of the lights.

Figure 17:
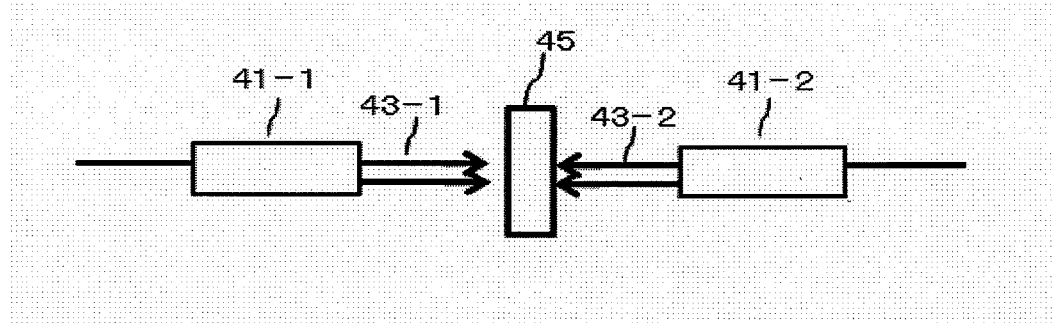
FIG. 17 illustrates an optical system as an embodiment of the present invention where a light-scattering specimen is inserted between opposing mode-matching polarized light converting collimators.
Figure 18:
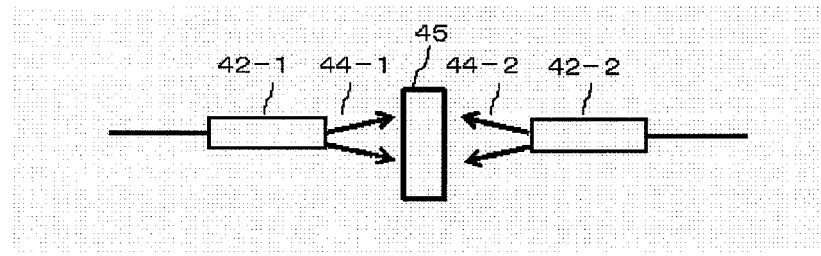
FIG. 18 illustrates an optical system as an embodiment of the present invention where a light-scattering specimen is inserted in opposing mode-matching/defocused polarized light converting optical systems.

FIG. 17 illustrates an optical system according to an embodiment of the present invention where a specimen 45 is inserted in an opposing mode-matching/polarized light converting collimator. FIG. 18 illustrates an optical system according to an embodiment of the present invention where the specimen 45 is inserted in an opposing mode-matching/defocused polarized light converting optical system.

In the case where the specimen 45 is a typical aqueous solution with low scattering loss, the opposing collimator of FIG. 17 has the smaller insertion loss. However, in the case where the specimen 45 is a light-scattering specimen such as a living body, as a result of various experiments by the inventor, the defocused polarized light converting optical system of FIG. 18 has approximately 1000 times (30 dB) smaller insertion loss than the opposing collimator system of FIG. 17. A simulation method for explaining the experiment results is not commercially available. Experiment results show that with the optical system of FIG. 14, the lowest insertion loss of 30 dB is achieved when the polarizer 38, the Faraday rotary element 39, and the ¼ wave plate 40 are made as thin as possible so as to approach the ends of the optical fibers and the lens 35. In addition, natural polarizing axis direction of opposing polarization-preserving fibers and natural polarizing axis direction of the opposing polarizer 38, the Faraday rotary element 39, and the ¼ wave plate are adjusted such that orthogonal circularly propagating polarized lights enter a living body from defocused polarized light converting optical systems 42-1 and 42-2 including a mode-matching unit of FIG. 18 deployed along an optical ring path of an optical interferometer described later, and once opposing linearly propagating polarized lights that propagate in both directions propagate through the specimen 45, the linearly polarized lights pass through the opposing defocused polarized light converting optical systems and couple with the same polarizing axis as the incident linearly-polarized lights.

Figure 19:
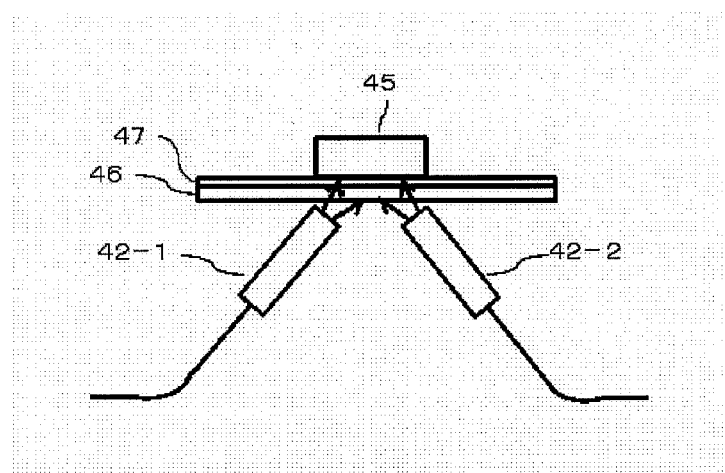
FIG. 19 is a diagram explaining a coupling optical system, as an embodiment of the present invention, for irradiating an optical signal obliquely onto a light-scattering specimen using mode-matching/defocused polarized light converting optical systems.

FIG. 19 is a diagram explaining a coupling optical system, according to an embodiment of the present invention, for irradiating an optical signal obliquely onto a light-scattering specimen using the defocused polarized light converting optical systems 42-1 and 42-2 including the mode-matching unit. FIG. 19 shows a reflection system opposed to the transmission system of FIG. 18. Reference numeral 46 denotes a silica glass plate, and 47 denotes a ¼ wave plate. Since the phase of light reflected on a living body surface or within a living body is generally inverted, when there is no phase plate, incident light and reflected light with respect to the living body become linearly propagating polarized lights, canceling out phase difference and thereby not allowing measurement of phase difference due to optical rotation of the living body. The same circularly propagating polarized light as the incident light is reflected by a phase plate (a type of mirror in this case) deployed between the living body and the incident light, thereby, along with the polarized state, coupling to the defocused polarized light converting optical systems 42-1 and 42-2 including the mode-matching unit. Note that the measurement system of FIG. 19 does not use a metal plate, and has a different principle than conventional surface plasmon resonance (SPR).

Figure 20:
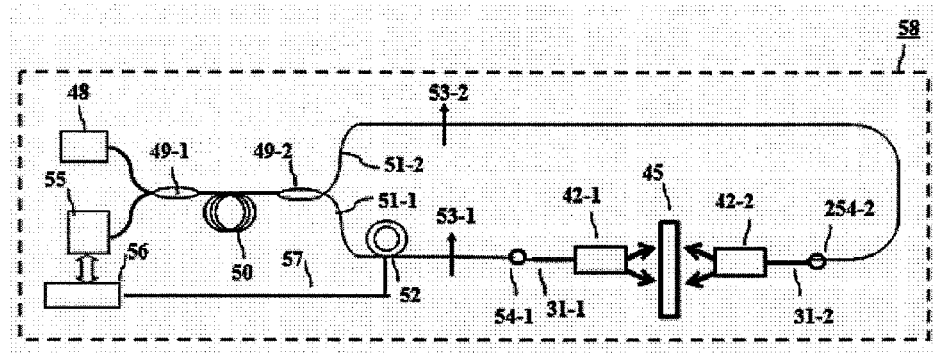
FIG. 20 illustrates a configuration of an optical rotation measurement apparatus, as an embodiment of the present invention, which uses a coupling optical system that sandwiches a light-scattering specimen by opposing mode-matching/polarized light converting optical systems.

FIG. 20 illustrates a configuration of principle parts 58 of an optical rotation measurement apparatus, according to an embodiment of the present invention, which has a coupling optical system that sandwiches a light-scattering specimen by opposing polarized light converting optical systems including the mode-matching unit deployed within an optical ring path including small core diameter high NA polarization preserving fibers 51-1 and 51-2 of an optical ring interferometer, and measures scattered light and reflected light from the surface or inside of the light-scattering specimen 45 as the specimen.

A light source 48 is a 1060 nm super luminescent diode (SLD), output thereof is led to a first directional coupler 49-1, an optical fiber polarizer 50, and a second directional coupler 49-2, and branched by the second directional coupler 49-2 into small core diameter high NA polarization preserving fibers 51-1 and 51-2 constituting an optical ring path, so as to generate clockwise and counterclockwise propagating linearly polarized lights 53-1 and 53-2 that propagate through the optical ring path. Reference numeral 52 denotes an optical phase modulator with an approximately 1 m-long small core diameter high NA polarization preserving fiber 51-1 wrapped around cylinder-type PZT (lead zirconate titanate). The clockwise and the counter-clockwise propagating light revolving through the optical ring path are connected to the defocused polarized light converting optical systems 42-1 and 42-2 including the mode-matching unit by splices 54-1 and 54-2, respectively. The lights scattered and reflected by the specimen 45 propagate through the opposing defocused polarized light converting optical systems 42-1 and 42-2, travel through the second coupler 49-2, the polarizer 50, and the first coupler 49-1, and are reconverted to electrical signals by a photo detector 55, so as for a signal processing unit 56 to calculate phase difference of the clockwise and the counter-clockwise propagating light from the optical rotation of the light-scattering specimen 45. A 20 KHz sinusoidal modulating signal 57 is applied to the optical phase modulator 52 from the signal processing unit 56. Directions of the linearly polarized lights 53-1 and 53-2 may be adjusted by turning an optical fiber around the optical axis so that the direction of polarization of the clockwise and counterclockwise propagating polarized lights entering the specimen cross each other.

Signal processing in FIG. 20 employs the method using a phase modulating system optical fiber gyro described in Non-patent Document 2. This is the same as in the case of phase modulation of FIG. 6.

In FIG. 20, the optical ring path of the ring light interference system is constituted mainly by the small core diameter high NA polarization preserving fibers 51-1 and 51-2, the defocused polarized light converting optical systems 42-1 and 42-2 described in the embodiments of the present invention, and the light-scattering specimen 45, which occupy most of a loop. A highly important point in FIG. 20 is that, as is understood from the description of the aforementioned embodiments, the clockwise and counter-clockwise propagating lights propagate as clockwise and counter-clockwise circularly propagating polarized lights, which are orthogonal to each other, only at the portion of the light-scattering specimen 45, and they propagate through the remaining portions of the respective polarization preserving fibers in the same natural polarization mode as the polarization preserving fibers. This allows stable measurement of only the phase difference of the clockwise and counter-clockwise propagating polarized lights in the light-scattering specimen. Generally, linearly propagating polarized light is broken down into clockwise and counter-clockwise propagating polarized lights, and when phase difference of 2θ occurs therebetween, direction of the polarized light changes by only θ. In FIG. 20, since phase difference between the clockwise and the counter-clockwise propagating polarized light in the light-scattering specimen 45 is possible, measurement of optic rotation is possible.

Next, experiment results of the case where the light-scattering specimen 45 as the specimen is webbing of fingers will be described. Thickness of a subject's skin is approximately 1.5 mm. If a polarization preserving fiber is deployed on either end thereof so as to sandwich the living body and optically couple them, insertion loss in the case of the opposing collimators of FIG. 17 is approximately 65 dB. However, the insertion loss is 35 dB in the case of the defocused opposing collimators of FIG. 18 that brought the large core diameter low NA optical fibers as close to the lens 35 as possible, and is even 30 dB less than in the aforementioned example. The levels of loss of the optical interference systems in this experiment are as given below.

Light source output: 10 mW (polarization-preserving fiber output)
Optical gyro (ring interference system) loss: 10 dB
Insertion loss of defocused polarized light converting/coupling optical systems sandwiching
living body: 34 dB
Mode-matching unit loss: 6 dB (2 places)
Connector and splice loss: 3 dB
Total loss: 53 dB
Light receiving power: 50 nW In this case, a photo detector uses a silicon avalanche photodiode (APD) having a minimum reception sensitivity of 5 pW at a bandwidth of 100 KHz. In this experiment, the large core diameter low NA polarization preserving fibers having a 30 μm core diameter are brought as close to the lens from the focal point as possible. Under such conditions, average measurement time is set to 10 seconds, and phase difference of the clockwise and counterclockwise propagating polarized lights transmitting through the webbing of fingers can be measured from a sufficient signal-to-noise ratio.

In this experiment, a refractive index matching material is applied on the webbing of the fingers so as to control reflection loss. Signals in sync with pulse beats are detected in this experiment. Phase difference is measured while shifting the measured region in a perpendicular direction to the optical axis. Phase difference varied according to region as a result. This is interpreted as resulting from difference in the cases of the beam propagating and not propagating through a blood vessel. Data on blood sugar can be obtained by repeating measurement of actual diabetic patients. Note that aside from detecting signals in sync with pulse beats, a method of applying periodical pressure on the sandwiching portion of the living body so as to periodically change the thickness of the living body, and detect periodical signals in sync with those periods is also effective. In addition, deploying a multimode optical fiber in parallel with the polarization preserving fiber for optical rotation measurement described with this invention near the region to be measured, and measuring fluctuation in insertion loss thereof allow measurement of pulse beats.

Figure 21:
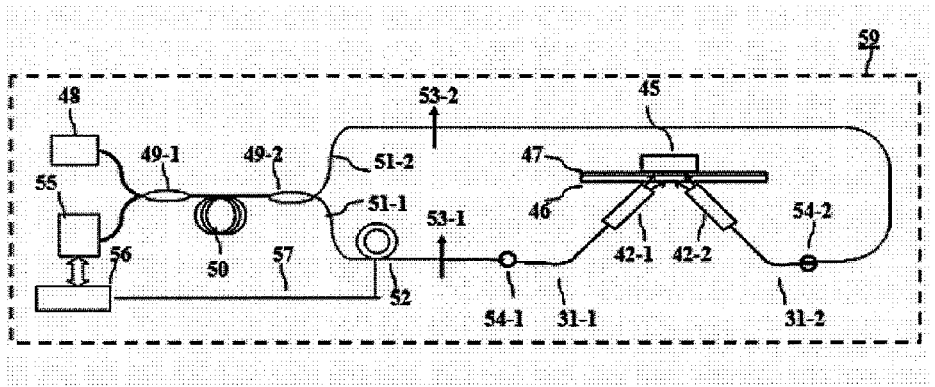
FIG. 21 illustrates a configuration of an optical rotation measurement apparatus, as an embodiment of the present invention, which uses a coupling optical system that irradiates an optical signal obliquely on a light-scattering specimen using opposing mode-matching/defocused polarized light converting optical systems.

FIG. 21 illustrates a configuration of principle parts 59 of an optical rotation measurement apparatus, as an embodiment of the present invention, having the coupling optical system of FIG. 19, which irradiates an optical signal obliquely on the light-scattering specimen 45 as the specimen using opposing mode-matching/defocused polarized light converting optical systems, deployed along the ring optical path of the ring interferometer, and measuring optical rotation of the light propagating on the surface of the light-scattering specimen. In this case, before arranging the light-scattering specimen 45, a mirror is placed at the specimen and axis adjustment is carried out so as to couple between the defocused polarized light converting optical systems 42-1 and 42-2 with necessary accuracy. Fingers are placed on the ¼ wave plate 47, and optical rotation included in reflected light and scattered light from the living body is then measured. A refractive index matching material is actually applied between the ¼ wave plate 47 and the fingers.

Even in this experiment, phase difference is measured while shifting the measured region on the flat surface of the ¼ wave plate 47. The phase difference varied according to region as a result. This is interpreted as resulting from difference in cases of the beam propagating and not propagating through a blood vessel. Measurement results may be displayed by creating data on blood sugar by repeating measurement of actual diabetic patients, creating a correspondence table of the measured data and blood sugar, for example, and entering it in a storage portion of a signal processing circuit 56, for example.

A preferred embodiment of the present invention is characterized in that at least either the one single mode optical fiber or the other single mode optical fiber has an output lens deployed at the tip end, and at least an end of the single mode optical fiber having the output lens constitutes a defocused polarized light converting optical system, which is an optical system not deployed at the focal point of the output lens.

Figure 22:
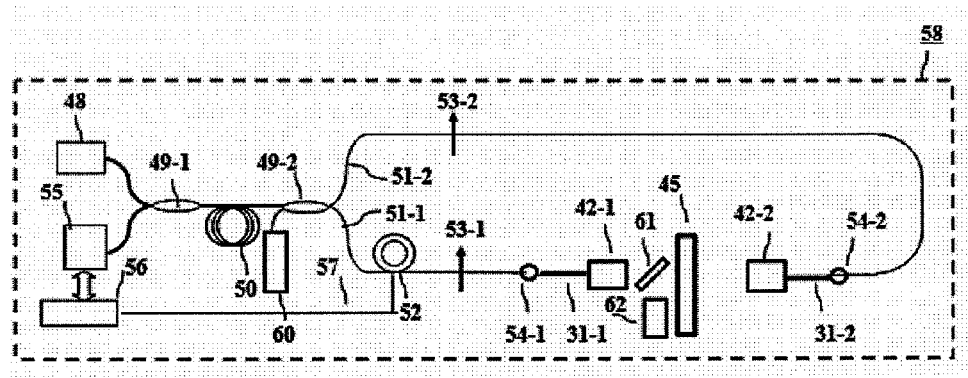
FIG. 22 is a diagram explaining a measurement method, as an embodiment of the present invention, for an optical rotation measurement apparatus.

FIG. 22 is a diagram explaining a measurement method, according to an embodiment of the present invention, for the principle parts 58 of an optical rotation measurement apparatus, and explains a method of observing what portion of the measured subject 45 is irradiated by a beam from the defocused polarized light converting optical system 42-1. That is, in actual measurement, a laser beam from a HeNe laser 60 as a visible laser enters from the other inlet end of the second coupler 49-2 of FIG. 22, a half mirror 61 is placed in front of the measured subject 45, and what portion of the measured subject 45 is irradiated by the beam emitted from the defocused polarized light converting optical system 42-1 is observed using a microscope 62. In the case where the specimen 45 is a living body, blood vessels could be observed by applying permeable oil. When measuring the optical rotation, the HeNe laser is turned off and the microscope and the half mirror are removed. Doing so clarified the positional relationship between optical rotation and blood vessel of the living body.

While the defocused optical rotation measurement apparatus, the defocused polarized light converting optical system, and the optical rotation measurement method using that optical system of the present invention are described above, the respective configurations according to the embodiments of the present invention may provide the results of the present invention even if they are used independently in the defocused optical rotation measurement apparatus, the defocused polarized light converting optical system, and the optical rotation measurement method using that optical system. Even if the present invention is constituted by various combinations thereof, it is not narrowly limited to only those combinations that can provide the results of the present invention, and many variations are possible based on the technical ideas of the present invention.

INDUSTRIAL APPLICABILITY

As described above, noninvasive blood sugar measurement that has not been available until now is possible according to the present invention. As a result, diabetic patients can be freed from the hassle of having blood drawn several times a day. Utilization of a blood sugar level measurement apparatus according to the present invention for preventive maintenance purposes allows reduction in the number of diabetic patients that is currently increasing worldwide, thereby substantially reducing required cost for this treatment. Moreover, the present invention is applicable in a wide range of fields, such as medical, nursing, health-care equipment, pharmaceuticals, food products, and agriculture.

The invention claimed is:

1. A defocused optical rotation measurement apparatus for measuring for optical information on optical rotation characteristics of a specimen by deploying single mode first and second optical fibers, each having a lens deployed at a tip end, along an optical path of an optical signal, facing each other and sandwiching the specimen for optical rotation measurement irradiating on the specimen an optical signal emitted from an end of the first single mode optical fiber having the lens at the tip end, and also irradiating on the specimen an optical signal emitted from an end of the second single mode optical fiber having the lens at the tip end, irradiating an optical signal having passed through the specimen and an optical signal reflected by the specimen on an end of the first single mode optical fiber having the lens at the tip end; wherein in a state of measuring optical rotation of the specimen, the lens deployed at an output part of the first single mode optical fiber for an optical signal irradiated on the specimen and/or an inlet part for an optical signal from the specimen, and the output part lens deployed at an inlet part of the second single mode optical fiber for an optical signal from the specimen and/or an output part for an optical signal irradiated on the specimen are deployed along the optical path of the optical signal, and at least either an end of the first single mode optical fiber or an end of the second single mode optical fiber forms a defocused optical fiber optical system not deployed at a focal point of the output part lens of said first and second single mode optical fibers;

wherein the first single mode optical fiber and the second single mode optical fiber are polarization preserving fibers; a polarizer, a Faraday rotary element, and a ¼ wave plate are arranged between each of the optical fiber ends and the specimen;

an optical signal of the same natural polarization mode is emitted from both of the polarization preserving fibers, a clockwise propagating light or a counterclockwise propagating light entering from one of the inlet sides of the specimen, and counterclockwise propagating light or a clockwise propagating light entering from the other one of the inlet sides of the specimen are mutually orthogonal at the position of the specimen, and directions of the polarizer, the Faraday rotary element, and the ¼ wave plate and a natural polarization direction of the polarization preserving fibers are set such that the lights are coupled with the polarization preserving fibers on an optical path in a polarization mode equivalent to the polarization output mode.

2. The defocused optical rotation measurement apparatus according to claim 1, wherein the end of the first single mode optical fiber and the end of the second single mode optical fiber are deployed at positions further away from the output part lenses of the optical fibers than focal points of the output part lenses.

3. The defocused optical rotation measurement apparatus according to claim 1, wherein the tip end of the first and second single mode optical fibers and the output part lens of the optical fibers are fixed to each other.

4. The defocused optical rotation measurement apparatus according to claim 1, wherein at least either the first single mode optical fiber or the second single mode optical fiber has a Faraday rotary element, a ¼ wave plate and a polarizer arranged between the specimen and the first and second single mode optical fibers end.

5. The defocused optical rotation measurement apparatus according to claim 4, wherein
both of the defocused optical fiber optical systems facing each other and sandwiching the specimen along the optical path of the optical signal and has the polarizer, the Faraday rotary element, the ¼ wave plate, and the output part lenses deployed at the optical fiber ends are on the same side of an optical signal inlet side, and the ¼ wave plate is deployed between the defocused optical fiber optical systems and the specimen.

6. The defocused optical rotation measurement apparatus according to claim 1, wherein
the specimen is a part of a living body, the defocused optical rotation measurement apparatus comprises measuring terminals for sandwiching a portion for measuring for optical information on optical rotation characteristics of the specimen, and the tip ends of the optical fibers are held by the measuring terminals.

7. The defocused optical rotation measurement apparatus according to claim 1, further comprising: an inter-lens distance adjusting means adjuster for changing distance between the output part lens of the first single mode optical fiber and the output part lens of the second single mode optical fiber.

8. The de focused optical rotation measurement apparatus according to claim 1, wherein at least either first single mode optical fiber or the second single mode optical fiber is an expanded-core fiber as a mode-matching unit having a larger core diameter and a lower numerical aperture in a portion closer to the specimen than those in a portion far away from the specimen.

9. The defocused optical rotation measurement apparatus according to claim 8, wherein
at least either an expanded-core fiber or a reduced-core fiber is used in the mode-matching unit.

10. The defocused optical rotation measurement apparatus according to claim 8, wherein the first single mode optical fiber and the second single mode optical fiber are polarization preserving fibers;
at least a part of an optical ring path a ring light interference system is constituted by the specimen, the defocused optical fiber optical system, and the polarization preserving fibers;
an optical signal of the same natural polarization mode is emitted from both of the polarization preserving fibers, and enters the specimen as either a clockwise propagating light or a counterclockwise propagating light from one of the inlet sides of the specimen, and enters the specimen as either a counterclockwise propagating light or a clockwise propagating light from the other one of the inlet sides of the specimen, where the clockwise propagating light or the counterclockwise propagating light entering from one of the inlet sides of the specimen, and the counterclockwise propagating light or the clockwise propagating light entering from the other one of the inlet sides of the specimen being mutually orthogonal at the position of the specimen;

a polarization direction of the optical signal is set such that the lights are coupled with the polarization preserving fibers on an optical path in a polarization mode equivalent to the polarization output mode; and optical rotation characteristics of the specimen is measured by measuring phase difference of the optical signal propagating along the optical ring path in both directions that occurs due to the specimen.

11. The defocused optical rotation measurement apparatus according to claim 8, further comprising:

a mechanism for scanning the specimen orthogonally to the optical path.

12. The defocused optical rotation measurement apparatus according to claim 8, wherein the specimen is a part of a living body, and the optical rotation measurement apparatus further comprises, as a part of detector for detecting the phase difference of the optical signals, a phase difference detector for detecting the phase difference in sync with pulse beats of the living body or with a technically applied signal for periodically varying dimensions of the part of the living body, such as thickness of a region to be measured, so as to measure optical information on optical rotation characteristics of the specimen.

13. A defocused optical fiber optical system used for an optical rotation measuring system, for measuring for optical information on optical rotation characteristics of a specimen by deploying single mode optical fibers, each having a lens deployed at a tip end, along an optical path of an optical signal, facing each other and sandwiching a specimen for optical rotation measurement irradiating on the specimen an optical signal emitted from an end of the first single mode optical fiber having the lens at the tip end, irradiating an optical signal having passed through the specimen or an optical signal reflected by the specimen on an end of the second single mode optical fiber having the lens at the tip end, and also irradiating on the specimen an optical signal emitted from an end of the second single mode optical fiber having the lens at the tip end, irradiating an optical signal having passed through the specimen and/or an optical signal reflected by the specimen on an end of the first and second single mode optical fibers having the lens at the tip end; wherein in a state of measuring optical rotation of the specimen, the lens deployed at an output part of the first and second single mode optical fibers for an optical signal irradiated on the specimen and/or an inlet part for an optical signal from the specimen, and the output part lens deployed at an inlet part of the first and second single mode optical fibers for an optical signal from the specimen and/or an output part for an optical signal irradiated on the specimen are deployed along the optical path of the optical signal, and at least either an end of the first single mode optical fiber or an end of the second single mode optical fiber is not deployed at a focal point of the output part lens of said single mode optical fiber;

wherein the first single mode optical fiber and the second single mode optical fiber are polarization preserving fibers; a polarizer, a Faraday rotary element, and a ¼ wave plate are arranged between each of the optical fiber ends and the specimen;

an optical signal of the same natural polarization mode is emitted from both of the polarization preserving fibers, a clockwise propagating light or a counterclockwise propagating light entering from one of the inlet sides of the specimen, and counterclockwise propagating light or a clockwise propagating light entering from the other one of the inlet sides of the specimen are mutually orthogonal at the position of the specimen, and directions of the polarizer, the Faraday rotary element, and the ¼ wave plate and a natural polarization direction of the polarization preserving fibers are set such that the lights are coupled with the polarization preserving fibers on an optical path in a polarization mode equivalent to the polarization output mode.

14. The defocused optical fiber optical system according to claim 13, wherein both of the defocused optical fiber optical systems facing each other and sandwiching the specimen along the optical path of the optical signal has the polarizer, the Faraday rotary element, the ¼ wave plate, and the output part lenses deployed at the optical fiber ends, which are on the same side of an optical signal inlet side, and a ¼ wave plate is deployed between the defocused optical fiber optical systems and the specimen.

15. The defocused optical fiber optical system according to claim 13, wherein by using a mode-matching unit, a single mode optical fibers used for either first single mode optical fiber or the second single mode optical fiber has a larger core diameter and a lower numerical aperture in a portion closer to the specimen than those in a portion far away from the specimen.

16. A defocused optical rotation measurement method for measuring for optical information on optical rotation characteristics of a specimen by deploying single mode optical fibers, each having a lens deployed at a tip end, along an optical path of an optical signal, facing each other and sandwiching a specimen for optical rotation measurement irradiating on the specimen an optical signal emitted from an end of the first single mode optical fiber having a lens at the tip end, irradiating an optical signal having passed through the specimen or an optical signal reflected by the specimen on an end of the second single mode optical fiber having the lens at the tip end, and also irradiating on the specimen an optical signal emitted from an end of the second single mode optical fiber having the lens at the tip end, irradiating an optical signal having passed through the specimen and/or an optical signal reflected by the specimen on an end of the first single mode optical fiber having the lens at the tip end; comprising the steps of forming, in a state of measuring optical rotation of the specimen, a defocused optical fiber optical system where at least either an end of the first single mode optical fiber or an end of the second single mode optical fiber is not deployed at a focal point of the output part lens of said single mode optical fiber, in which the lens deployed at an output part of the first single mode optical fiber for an optical signal irradiated on the specimen and/or an inlet part for an optical signal from the specimen, and the output part lens deployed at an inlet part of the second single mode optical fiber for an optical signal from the specimen and/or an output part for an optical signal irradiated on the specimen are deployed along the optical path of the optical signal; and forming, by using a mode-matching unit, at least either the first single mode optical fiber or the second single mode optical fiber to have a larger core diameter and a lower numerical aperture in a portion closer to the specimen than those in a portion far away from the specimen;

wherein the first single mode optical fiber and the second single mode optical fiber are polarization preserving fibers; a polarizer, a Faraday rotary element, and a ¼ wave plate are arranged between each of the optical fiber ends and the specimen;

an optical signal of the same natural polarization mode is emitted from both of the polarization preserving fibers, a clockwise propagating light or a counterclockwise propagating light entering from one of the inlet sides of the specimen, and counterclockwise propagating light or a clockwise propagating light entering from the other one of the inlet sides of the specimen are mutually orthogonal at the position of the specimen, and directions of the polarizer, the Faraday rotary element, and the ¼ wave plate and a natural polarization direction of the polarization preserving fibers are set such that the lights are coupled with the polarization preserving fibers on an optical path in a polarization mode equivalent to the polarization output mode.

17. The defocused optical rotation measurement method according to claim 16, further comprising a step of scanning the specimen orthogonally to the optical path.

18. The defocused optical rotation measurement method according to claim 16, further comprising a step of arranging both of the defocused optical fiber optical systems facing each other and sandwiching the specimen along the optical path of the optical signal to have a polarizer, a Faraday rotary element, a ¼ wave plate, and the output part lenses deployed at the optical fiber ends, which are on the same side of an optical signal inlet side, and a ¼ wave plate is deployed between the defocused optical fiber optical systems and the specimen.

19. An optical rotation measurement apparatus for measuring for optical information on optical rotation characteristics of a specimen by deploying single mode optical fibers, each having a lens deployed at a tip end, along an optical path of an optical signal, facing each other and sandwiching a specimen for optical rotation measurement, irradiating on the specimen an optical signal emitted from an end of the first single mode optical fiber having the lens at the tip end, irradiating an optical signal having passed through the specimen and/or an optical signal reflected by the specimen on an end of the other single mode optical fiber having the lens at the tip end, and also irradiating on the specimen an optical signal emitted from an end of the second single mode optical fiber having the lens at the tip end, irradiating an optical signal having passed through the specimen and/or an optical signal reflected by the specimen on an end of the first single mode optical fiber having the lens at the tip end; wherein at least either the first single mode optical fiber or the second single mode optical fiber is an expanded-core fiber as a modematching unit, having a larger core diameter and a lower numerical aperture in a portion closer to the specimen than those in a portion far away from the specimen;

wherein the first single mode optical fiber and the second single mode optical fiber are polarization preserving fibers; a polarizer, a Faraday rotary element, and a ¼ wave plate are arranged between each of the optical fiber ends and the specimen;

an optical signal of the same natural polarization mode is emitted from both of the polarization preserving fibers, a clockwise propagating light or a counterclockwise propagating light entering from one of the inlet sides of the specimen, and counterclockwise propagating light or a clockwise propagating light entering from the other one of the inlet sides of the specimen are mutually orthogonal at the position of the specimen, and directions of the polarizer, the Faraday rotary element, and the ¼ wave plate and a natural polarization direction of the polarization preserving fibers are set such that the lights are coupled with the polarization preserving fibers on an optical path in a polarization mode equivalent to the polarization output mode.

\* \* \* \* \*